(12) United States Patent
Sagi et al.

(10) Patent No.: US 8,440,878 B2
(45) Date of Patent: May 14, 2013

(54) INSULIN-LIKE GENE IN PRAWNS AND USES THEREOF

(75) Inventors: Amir Sagi, Omer (IL); Tomer Ventura, Beer Sheva (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 8 days.

(21) Appl. No.: 13/277,088

(22) Filed: Oct. 19, 2011

(65) Prior Publication Data
US 2012/0073508 A1 Mar. 29, 2012

Related U.S. Application Data

(63) Continuation-in-part of application No. 12/865,854, filed as application No. PCT/IL2009/000127 on Feb. 4, 2009.

(60) Provisional application No. 61/025,831, filed on Feb. 4, 2008.

(51) Int. Cl.
*A01K 67/027* (2006.01)
*C12N 15/00* (2006.01)
*C12N 15/11* (2006.01)

(52) U.S. Cl.
USPC .............................. 800/20; 800/21; 514/44 A

(58) Field of Classification Search .................. None
See application file for complete search history.

(56) References Cited

U.S. PATENT DOCUMENTS

| | | | |
|---|---|---|---|
| 6,740,794 B1 | 5/2004 | Malecha | |
| 2005/0080032 A1 | 4/2005 | Gross | |

FOREIGN PATENT DOCUMENTS

| | | |
|---|---|---|
| CN | 1075983 | 9/1993 |
| CN | 101029077 | 9/2010 |
| WO | 2004/085645 A1 | 10/2004 |
| WO | 2007/122247 A1 | 11/2007 |

OTHER PUBLICATIONS

Chung, J. Sook et al., "Cloning of an insulin-like androgenic gland factor (IAG) from the blue crab, *Callinectes sapidus*: implications for eyestalk regulation of IAG expression", Gen Comp Endocrinol, 173(1):4-10 (2011).
Duret, Laurent et al., "New insulin-like proteins with atypical disulfide bond pattern characterized in *Caenorhabditis elegans* by comparative sequence analysis and homology modeling", Genome Res., 8(4):348-353 (1998).
Ebberink, R. H. M. et al., "The Insulin Family: Evolution of Structure and Function in Vertebrates and Invertebrates", Biol Bull., 177(2):176-182 (1989).
Manor, Rivka et al., "Insulin and gender: an insulin-like gene expressed exclusively in the androgenic gland of the male crayfish", Gen Comp Endocrinol, 150(2):326-336 (2007).
Mareddy, V. R. et al., "Isolation and characterization of the complete cDNA sequence encoding a putative insulin-like peptide from the androgenic gland of *Penaeus monodon*", Aquaculture, 318(3-4):364-376 (2011).
Ohira, Tsuyoshi et al., "Molecular cloning and expression analysis of cDNAs encoding androgenic gland hormone precursors from two porcellionidae species, *Porcellio scaber* and *P. dilatatus*", Zoolog Sci., 20(1):75-81 (2003).
Riehle, Michael A. et al., "Molecular characterization of insulin-like peptides in the yellow fever mosquito, *Aedes aegypti*: expression, cellular localization, and phylogeny", Peptides, 27(11):2547-2560 (2006).
Shechter, Asaf et al., "Expression of the reproductive female-specific vitellogenin gene in endocrinologically induced male and intersex *Cherax quadricarinatus* crayfish", Biol Reprod., 73(1):72-79 (2005).
Smit, A. B. et al., "Expression and characterization of molluscan insulin-related peptide VII from the mollusc *Lymnaea stagnalis*", Neuroscience, 70(2):589-596 (1996).
Staelens, Jan et al., "High-density linkage maps and sex-linked markers for the black tiger shrimp (*Penaeus monodon*)", Genetics, 179(2):917-925 (2008).
Sun, Piera S. et al., "Developmental changes in structure and polypeptide profile of the androgenic gland of the freshwater prawn *Macrobrachium rosenbergii*", Aquaculture International, 8(4):327-334 (2000).
Thompson, Julie D. et al., "Clustal W: improving the sensitivity of progressive multiple sequence alignment through sequence weighting, position-specific gap penalties and weight matrix choice", Nucleic Acids Res., 22(22):4673-4680 (1994).
Ventura, Tomer, "Temporal Silencing of an Androgenic Gland-Specific Insulin-Like Gene Affecting Phenotypical Gender Differences and Spermatogenesis", Endocrinology, 150(3):1278-1286 (2009).
Ventura, T. et al., "Isolation and characterization of a female-specific DNA marker in the giant freshwater prawn *Macrobrachium rosenbergii*", Heredity (edinb), 107(5):456-461 (2011).
Ventura, Tomer et al., "Expression of an Androgenic Gland-Specific Insulin-Like Peptide during the Course of Prawn Sexual and Morphotypic Differentiation", ISRN Endocrinology, 2011:476283 (2011).
Watson, J. D. and Crick, F. H., "Molecular structure of nucleic acids; a structure for deoxyribose nucleic acid", Nature, 171(4356):737-738 (1953).
U.S. Appl. No. 12/865,854 Request for Restriction/Election dated Feb. 22, 2012.
U.S. Appl. No. 12/865,854 Non-Final Rejection dated Apr. 27, 2012.
Chinese Search Report from corresponding Chinese Application No. 2009801111600 dated Nov. 16, 2012 (3 pages).

*Primary Examiner* — Valarie Bertoglio
(74) *Attorney, Agent, or Firm* — Rodney J. Fuller; Booth Udall Fuller, PLC

(57) ABSTRACT

The present invention relates to a nucleic acid molecule encoding an insulin-like factor of the androgenic gland of the freshwater prawn *Macrobrachium rosenbergii* (*M. rosenbergii*). The present invention further relates to methods of silencing the expression of the insulin-like factor gene in decapod crustaceans order, particularly in *M. rosenbergii*, useful for producing male monosex populations.

10 Claims, 16 Drawing Sheets

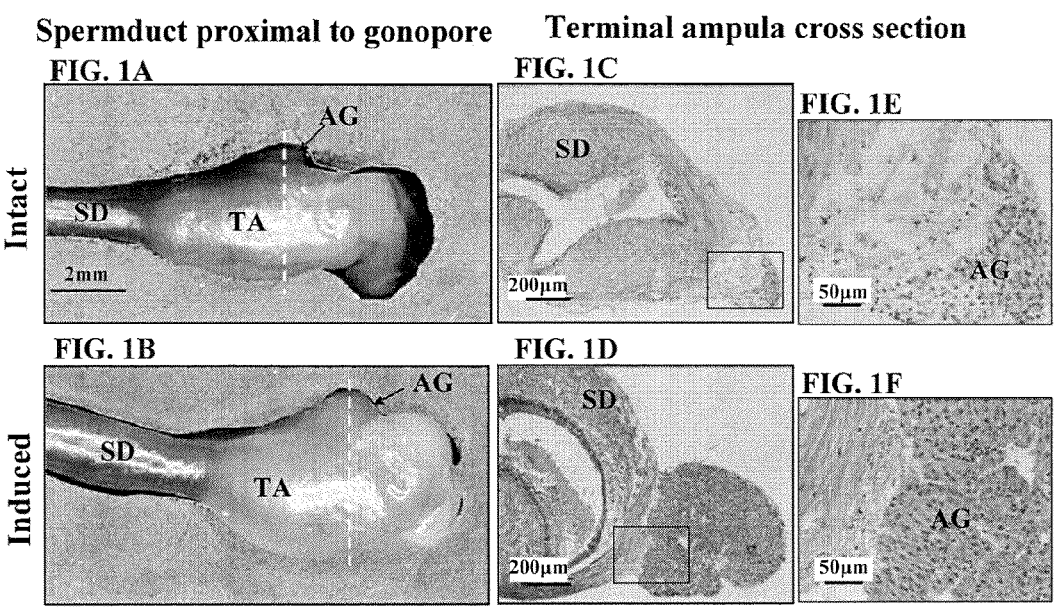

```
nt 1      GGTTATTCCAAGAGGGGCCAAGACTCTGGGATCACACCTCGAACGGCTCTGTCCCTTCCC
nt 61     CTCGTCCGTTTAACCGGTGTTTTCTAGCCACGCTCTCAACACCTAAAAATTCCCTCTCTT
nt 121    GCTTTCTGGCCAGCCTTGCAGTCATCCTTGAAATTCCCTCTTCCTTATATTTCGGGACAT
nt 181    AACATTCTTCTCTCCGGCCTTTTCATATCGAAGTGAAACAAATCAACTACAGAATGGGAT
aa 1                                                                M  G  Y
nt 241    ACTGGAATGCCGAGATCAAGTGTGTGTTGTTCTGCTCACTCGTAGCATCGCTTCTCCCTC
aa 4       W  N  A  E  I  K  C  V  L  F  C  S  L  V  A  S  L  L  P  Q
nt 301    AACCTTCTTCGAGCTATGAGATCGAATGCCTCTCCGTTGACTTTGACTGCGGCGACATAA
aa 24      P  S  S  S  Y  E  I  E  C  L  S  V  D  F  D  C  G  D  I  T
nt 361    CGAACACCCTTGCCTCCGTCTGCCTGAGACACAACAACTACATCAACCCAGGACCCACCT
aa 44      N  T  L  A  S  V  C  L  R  H  N  N  Y  I  N  P  G  P  T  Y
nt 421    ACGTTTCCAAAGAGCGACGATCTGCTGACATCTATACCGTTCCTTCTACGAAGTCTCCAT
aa 64      V  S  K  E [R  R] S  A  D  I  Y  T  V  P  S  T  K  S  P  S
nt 481    CGCTCGCCCACCCGAGACGTACCCACTTGACCATGGCTGACGAAGAAACTCAGAAGGTAT
aa 84      L  A  H  P  R  A  T  H  L  T  M  A  D  E  E  T  Q  K  V  S
nt 541    CTAAGGTGGAGGAGGAGATTCAGCACATGACGCTGAGCAGGGAAGAAGCGAACAATATGC
aa 104     K  V  E  E  E  I  Q  H  M  T  L  S  R  E  E  A  N  N  M  L
nt 601    TGCATTCGAAGCGTCGCTTCCGGAGGGACAGCGTGAGGAGAAGTCCAAGGGAGGAATGCT
aa 124     H  S [K  R] R  F  R  R  D  S  V  R  R  S  P  R  E  E  C  C
nt 661    GCAACAACGCCTCTTTCAGACGCTGCAACTTCGAGGAAGTCGCCGAATATTGCATCGAGC
aa 144     N  N  A  S  F  R  R  C  N  F  E  E  V  A  E  Y  C  I  E  L
nt 721    TGCGTCCCGGCGTTAACACCTGCAGTTCCAGGTAGGAGGTCTCAAGGATCATCCCGTCCC
aa 164     R  P  G  V  N  T  C  S  S  R  *
nt 781    TGTCCTATACTTGACAGGAGATGCTCAAAGTCAAATCACCGTCTTCGAGTCATGATGTGG
nt 841    AATGACCTTCAGCTAAAGCTGCCTTTTGGCTTTCCTCACAGTCAACTAAAAACAATTTTT
nt 901    TTTATCCTACCGTTACCTTCAGATAAATTATTCCTTTGTCTCAGCTTTAATTTCGGCTAA
nt 961    AGCTTTTTTTTTGTTCTACCCATGCATTCAGCTAAAGCTTTCTTTTGTTTCGCCTTTAA
nt 1021   ATTCAACACTCCTCTGCCTTACCCTTATTTCAGCTAATGGCTTCTTTTTATTTTACCATT
nt 1081   ACCATCCACAAAGCTTTGTTTTGTCTTACCCTCAGCTGAAACGTTTGTTTGTCTCACCTT
nt 1141   TACCCTCAGCTAAAACTTTCTTTTGTCTTCCCGCTGCTTTAGTAAATGCTTTCTTCTGTC
nt 1201   ACACTTTTACTTTCAGCTAGGGATTCTTTTTTTTTTTGCCACTTTTACCTTCAGCTAA
nt 1261   AGGGTACTATTGTCTCACCCTTGCCTTCTGCTAAAGGTTCCTTTTGTCCCACCCTTGCCT
nt 1321   TCAACTAAAGGTTCCTTTTGTCTCACCCTTGCCTTCAGCTAAAGGTTCCTTTTGTCTCAC
nt 1381   CCTTGCCTTCAGCTAAAGGTTCCTTTTGTCTCACCCTTGCCTTCAGCCAAAGGTTCCTTT
nt 1441   TGTCTCACCCTTGCCTTCAGCTAAAGGTTCCATTTGTCTCACCTTTGCCTTCAGCTAAAG
nt 1501   GTTCCTTTTGTCTCACCCTTGCCTTCAGCTAAAGGTCCCTTTTGTCTCACCCGTGCATCC
nt 1561   AACTAAAGGTTCCTTTTACCTCTCTTTTATCTTTAACTAAAGTTTTTTGTTTTTGTATCC
nt 1621   TTGCCTTCAGCCAAACGTTCTTTTGTTTTATCTTTACACGCAACAACATCTAGACATTTC
nt 1681   CAAACATTAAGCATATTGCATTATTATTGGTGATTCTTGTCGATGTTTCCGAAAAATTGT
nt 1741   TTGATACATCAGTTATACGTCAAATAAATGCTTTTGAGAACCCGGAAAAAAAAAAGAAA
nt 1801   AAAAAAAAAAAAAAAAAAAAAAAA
```

FIG. 2

```
ATGGGATACTGGAATGCCGAGATCAAGTGTGTGTTGTTCTGCTCACTCGTAGCATCGCTT
CTCCCTCAACCTTCTTCGAGCTATGAGATCGAATGCCTCTCCGTTGACTTTGACTGCGGC
GACATAACGAACACCCTTGCCTCCGTCTGCCTGAGACACAACAACTACATCAACCCAGGA
CCCACCTACGTTTCCAAAGAGCGACGATCTGCTGACATCTATACCGTTCCTTCTACGAAG
TCTCCATCGCTCGCCCACCCGAGAGCTACCCACTTGACCATGGCTGACGAAGAAACTCAG
AAGGTATCTAAGGTGGAGGAGGAGATTCAGCACATGACGCTGAGCAGGGAAGAAGCGAAC
AATATGCTGCATTCGAAGCGTCGCTTCCGGAGGGACAGCGTGAGGAGAAGTCCAAGGGAG
GAATGCTGCAACAACGCCTCTTTCAGACGCTGCAACTTCGAGGAAGTCGCCGAATATTGC
ATCGAGCTGCGTCCCGGCGTTAACACCTGCAGTTCCAGG
```

FIG. 3

B chain

```
Mr-IAG    YEIECLSVDFDCGDITNTLASVCLR---H--NNYINPGPTYVSKERR  42
Cd-IAG    YRVDNLLIDFDCGHLADTMDSICRT---Y--KEEND------TRAVR  36
Cq-IAG    YRVENLLIDFDCGHLADTMDSICRT---Y--QEEND------TRAVR  36
Arv-AGH   YQVRGMRSDVLCGDIRFTVQCICNELGYFPTERLDKPCP-WPNREKR  46
Pod-AGH   YQVEGMKSDVICADIRFTVHCICNELGRFPTARLTKPCP-WPNRERR  46
Pos-AGH   YQVIGMKSDVICADIRFTVHCICNELGLFPTSRLSKPCP-WPNRGRR  46
```

A chain

```
Mr-IAG    --RFRRDSVRRSPREECCNNASFRRCMFEEVAEYCIELRPGVNTCSSR  46
Cd-IAG    DSDTTDNTSSTNVYDECCSEKTLKTCVFDEIAQYCEQLEDGIYV-SS-  46
Cq-IAG    NSDTTDNTSSTNVYDECCSEKTLKTCVFDEIAQYCEQLEDGIYV-SS-  46
Arv-AGH   ---------EIAFYQECCNIRTEHKCNRTTVSLYCRTY---------  29
Pod-AGH   ---------DIAFHEECCNIRTEHKCNRTTVELYCRRYSP--------  31
Pos-AGH   ---------DIAFHEECCNIRTEHKCNKTTVELYCRRYTR--------  31
```

FIG. 4A

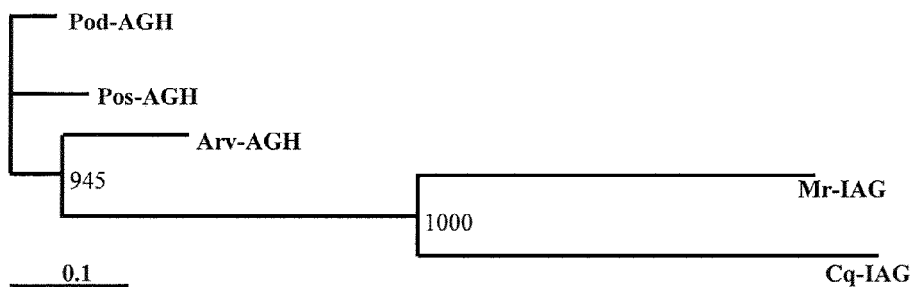

FIG. 4B

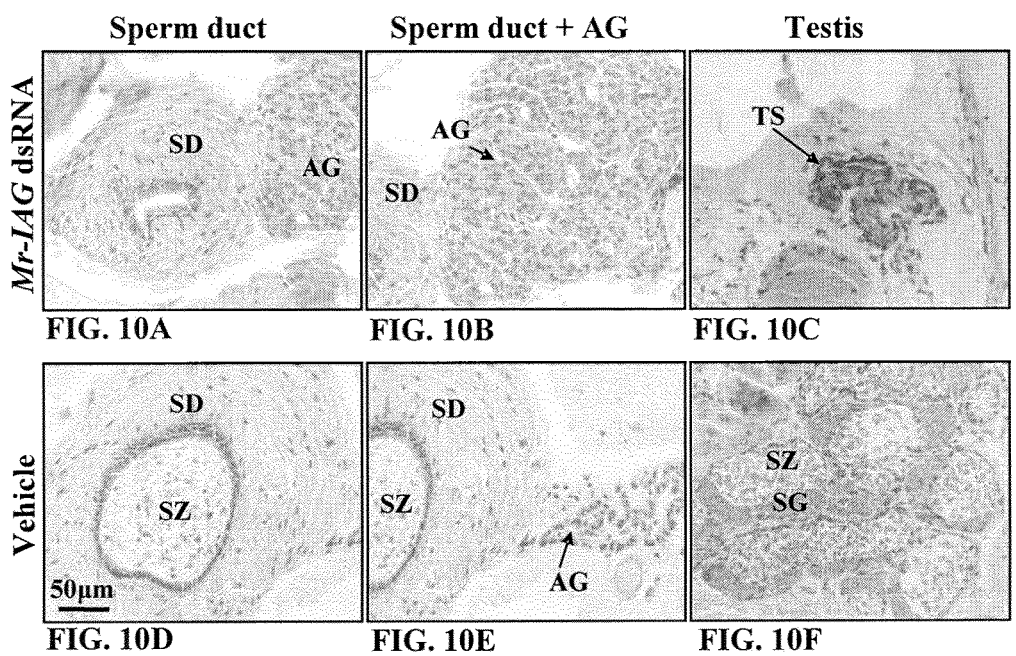

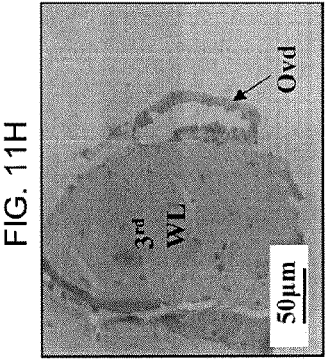
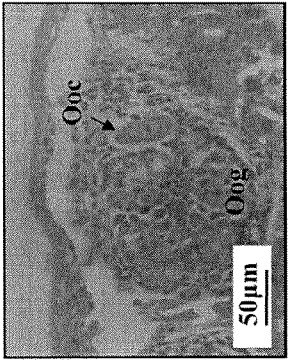
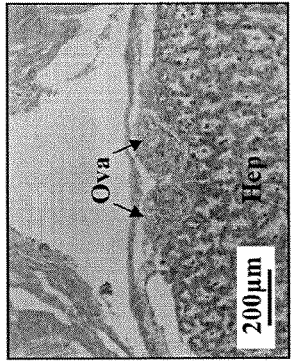
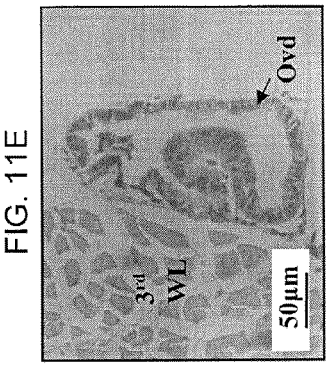
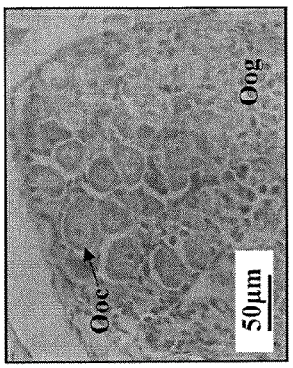
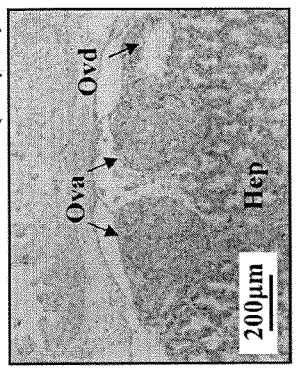
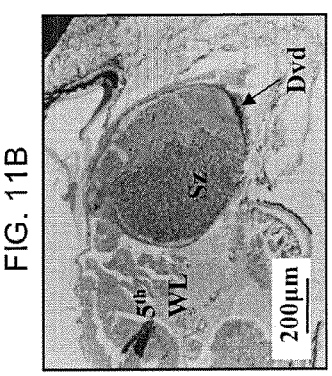
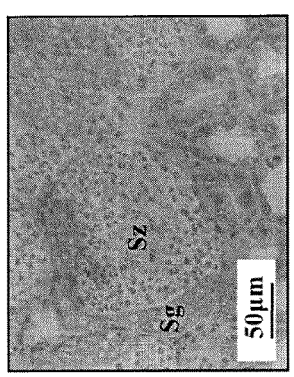
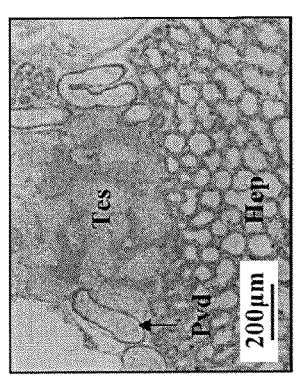

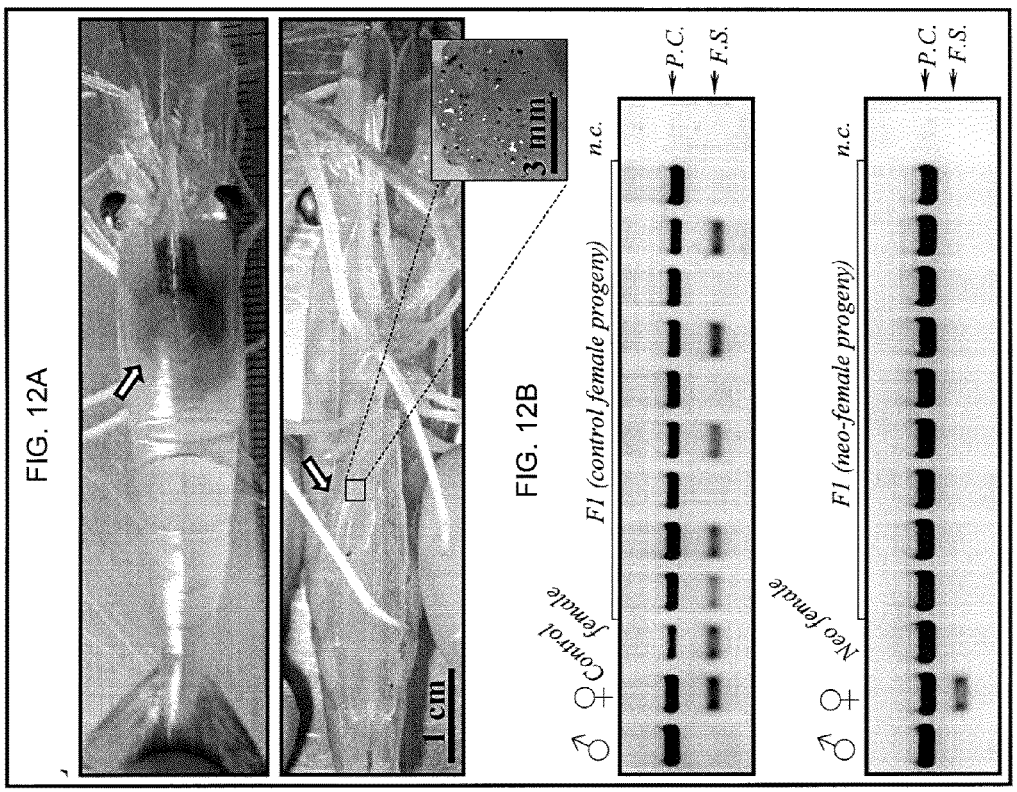

INSULIN-LIKE GENE IN PRAWNS AND USES THEREOF

CROSS-REFERENCE TO RELATED APPLICATIONS

This application is a Continuation-in-Part of U.S. application Ser. No. 12/865,854 filed Aug. 2, 2010, which is a U.S. National Stage application of PCT/IL2009/000127 filed Feb. 4, 2009, which is a non-provisional of and claims the benefit of U.S. provisional Application No. 61/025,831 filed Feb. 4, 2008, the contents of each of which are herein incorporated by reference for all purposes.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 13,665 byte ASCII (text) file named "Seq_List" created on Oct. 19, 2011.

FIELD OF THE INVENTION

The present invention relates to a nucleic acid molecule encoding an insulin-like factor of the androgenic gland of the freshwater prawn *Macrobrachium rosenbergii* (*M. rosenbergii*). The present invention further relates to methods of silencing the expression of the insulin-like factor gene in organisms of the decapod crustacean order, particularly in *M. rosenbergii*, useful for producing male monosex populations.

BACKGROUND OF THE INVENTION

Sexual differentiation and the development of secondary sexual characteristics are controlled by different mechanisms across evolution. In vertebrates and some invertebrate groups, these processes are under the control of sex hormones. Given the recent confirmation that insects probably have no sex hormones, the agents responsible for the sexual maturation of arthropods remain under debate. Crustaceans that are evolutionary close to insects possess an androgenic gland (AG) which is responsible for male sexual differentiation.

The role of the AG in male sexual differentiation was demonstrated in several crustacean species by observing primary and secondary sex characteristics after AG removal or transplantation. In the amphipod *Orchestia gamarella*, bilateral AG ablation diminished spermatogenesis and obstructed the development of secondary male characteristics. In the crayfish *Procambarus clarkii*, injection of AG extracts protruded external male characteristics. In *Macrobrachium rosenbergii*, a fully functional sex reversal from males to neo-females and from females to neo-males was achieved by bilateral AG ablation and transplantation, respectively.

The first AG hormone and its two closely related orthologs were found in isopods to be members of the insulin family of hormones as they possess B and A chains with a conserved cysteine residues skeleton, separated by a C peptide present in the pre-hormone and cleaved to give rise to the mature hormone (Ohira et al., Zoolog. Sci. 20: 75-81, 2003).

The insulin-like family of peptides is diverse and widespread. Many multi-cellular organisms were shown to differentially express several different insulin-like peptides. The insulin-like peptides discovered in invertebrates are not confined to glucose metabolism and have roles in metabolism, growth and reproduction. The silkworm *Bombyx mori* has three insulin-like prothoracicotropic hormones expressed in its brain (Bombyxin I, II and III) regulating ecdysteroids level (Ebbernick et al., Biol. Bull. 177: 176-182, 1989). The freshwater snail *Lymnaea stagnalis* retains seven insulin-like growth factors expressed in its brain and digestive system, functioning in shell and body growth as well as energy metabolism (Smit et al., Neurosci. 70: 589-596, 1996). In the nematode *Caenorhabditis elegans* ten insulin-like peptides were divided into three distinct families. Insulin-like peptides from two of these families probably comprise an additional disulfide bond (Duret et al. Genome Res. 8: 348-353, 1998), as is suggested to be the case for the three isopod insulin-like AG factors. Most insulin-like genes, not including insulin-like growth factors, encode a single pre-pro-peptide with a signal peptide and contiguous B, C, and A peptides. The pro-peptide is processed into an active form by linkage of the A and B peptides by disulfide bridges followed by proteolytic cleavage of the C peptide (Riehle et al., Peptides 27: 2547-2560, 2006).

Since the AG has an enormous effect on primary and secondary male characteristics in decapod crustaceans, it is considered not only as a male sex differentiation regulating organ but also as an organ responsible for maintenance of male morphological features. In *M. rosenbergii* there are three distinct mature male morphotypes, differing in behavior and growth rate. The larger, dominant blue claw (BC) males actively court and protect the females prior to mating. The orange claw (OC) males demonstrate reduced rate of reproductive activities in the presence of dominant males and the small males (SM) practice a form of sneak mating consistent with their small size and higher mobility. An anatomical study demonstrating high gonado-somatic index in BC and SM supported their more intense reproductive behavior compared with OC males which demonstrate poor reproductive skills and invest more effort in somatic growth. In *M. rosenbergii*, removal of AG from OC males caused attenuation of their transformation to the BC male morphotype, compared with sham operated OC males. The same procedure in SM arrested the dissected individuals in the OC male morphotype. Sun et al. (Aquaculture Internation. 8: 329-334, 1996) found that AG total polypeptide content increased gradually among the male morphotypes with the highest polypeptide content found in BC males. Sun further hypothesized that two polypeptides with apparent molecular weight of ~16 and ~18 kDa might be the AG hormone based on size similarity to the AG hormone found in Isopoda and reported the absence of these polypeptides in sexually inactive OC morphotype and presence in sexually active male morphotypes. However, in this study no AG-specific substance was extracted that could be considered as an AG hormone Manor et al. (Gen. Comp. Endocrin. 150:326-336, 2007) reported the identification of an AG-specific gene, termed Cq-IAG, in the decapod red-claw crayfish *Cherax quadricarinatus*. Cq-IAG was shown to be expressed exclusively in AG and its deduced protein was found to be similar in its cysteine backbone and 3D structure to the insulin-like family members (Manor et al., ibid).

U.S. Pat. No. 6,740,794 to Malecha et al. discloses several unidentified polypeptides with apparent molecular weights of 8, 13, 14, 16, 18, and 23-26 kDa obtained from the AG of male prawn *M. rosenbergii*. Two of these polypeptides, the 16 and 18 kDa, were presumed to be the androgenic sex hormone (AH). However, in this study too, no AG-specific substance was extracted that could be considered as an AG hormone U.S. Pat. No. 6,740,794 further discloses uses of AH in treating genetic female shrimp or prawns to produce neomales which can mate with genotypic females to produce female mono-sex shrimp or prawn progeny. U.S. Pat. No. 6,740,794 teaches the advantage of treating female shrimp or prawn with AH as such treatment produces populations of female shrimps and freshwater prawns (*M. rosenbergii*) having a significant economic advantage over their male counterparts.

U.S. Patent Application Publication No. 2005/0080032 discloses methods for inducing systemic, non-specific, and/or sequence specific immune responses in invertebrates comprising administering to the invertebrate at least one dsRNA that confers immunity against a pathogen, particularly a virus, or modulates expression of a gene that affects growth, reproduction, and general health. Two genes are specifically studied in U.S. Patent Application Publication No. 2005/0080032, a STAT-like gene and an I-KB-Kinase like gene (IKK); both were selected because of the known role of their orthologs in immune responses. U.S. Patent Application Publication No. 2005/0080032 neither discloses nor suggests silencing of a specific insulin-like peptide in invertebrates.

Several crustacean species including the freshwater giant prawn *M. rosenbergii* exhibit a bimodal growth pattern in which males exhibit superior growth to females. It was shown that in comparison to all-female *M. rosenbergii* populations, all-male *M. rosenbergii* populations produce higher marketable yields, grow faster and thus require shorter periods of time to harvest, and give higher income per unit area. The means to produce male monosex *M. rosenbergii* populations were found to be inefficient and involve tedious procedures such as manual segregation and microsurgical removal of AG from immature males, both procedures require high technical skills (Aflalo et al., 2006, Sagi et al., 1986 and Nair et al., 2006).

There is still a need for efficient, technically improved and economically beneficial methods to produce male monosex populations of decapod crustaceans, particularly of *M. rosenbergii*.

SUMMARY OF THE INVENTION

The present invention provides for the first time a nucleic acid molecule comprising the nucleotide sequence as set forth in SEQ ID NO:1 which encodes an insulin-like factor specifically expressed in the androgenic gland (AG) of the decapod *Macrobrachium rosenbergii* (*M. rosenbergii*). The present invention further provides the deduced amino acid sequence of the insulin-like factor expressed in the AG of *M. rosenbergii*.

It is now disclosed that the insulin-like factor gene is differentially expressed in the AG of male morphotypes of *M. rosenbergii*, i.e., its expression level is high in the reproductively active blue claw and small males while it is lower in the less reproductively active orange claw males.

It is further disclosed that administering to post-larvae *M. rosenbergii* males double stranded RNAs, in which one of the strands comprises a nucleotide sequence that is complementary to at least a portion of the open reading frame of an insulin-like factor gene of the AG of *M. rosenbergii*, resulted in silencing the expression of the insulin-like factor gene in these *M. rosenbergii* freshwater prawns. The silencing of the expression of the insulin-like factor gene in *M. rosenbergii* males caused prevention of the regeneration of the appendix masculina (AM) and inhibition of spermatogenesis which was accompanied by a lag in molt intervals and a reduction in weight accumulation.

It is further discloses that not only that the appearance of the external male sexual characteristics such as appendix masculina (AM) was inhibited by the silencing of the expression of the insulin-like factor gene (MG), the *M. rosenbergii* IAG-silenced males developed ovaries and oviducts.

Thus, the silencing of the insulin-like factor gene in *M. rosenbergii* freshwater prawn males lead to complete and irreversible functional sex reversal from males to neofemales, i.e., males genetically, but females phenotypically. Moreover, mating of *M. rosenbergii* neofemales (in which the MG was silenced) with males resulted in all male progeny.

The present invention thus provides methods for silencing the expression of the insulin-like factor gene in decapod crustaceans, particularly in *M. rosenbergii* males (genetically), thereby producing monosex male populations. As male decapod *M. rosenbergii* freshwater prawns grow faster and gain higher body weight than female freshwater prawns, the present invention provides means to produce large quantities of male freshwater prawns at significantly shorter periods of time.

According to one aspect, the present invention provides a nucleic acid molecule comprising the nucleotide sequence as set forth in SEQ ID NO:1 (designated herein Mr-IAG) encoding an insulin-like factor originated from the androgenic gland of *M. rosenbergii*, or a complementary strand, homolog or fragment thereof, wherein the homolog has sequence identity of at least 70% to SEQ ID NO:1. It is to be understood that SEQ ID NO:1 has 1824 nucleotides in length. According to some embodiments, the homolog has sequence identity of at least 80% to SEQ ID NO:1, alternatively of at least 90%, 95%, or of at least 99% sequence identity to SEQ ID NO:1. According to one embodiment, the fragment of the nucleic acid molecule comprises the nucleotide sequence as set forth in SEQ ID NO:2, i.e., the open reading frame of Mr-IAG encoding the pre-pro-hormone form of the insulin-like factor originated from the androgenic gland of *M. rosenbergii*, or a homolog thereof. It is to be understood that SEQ ID NO:2 has 519 nucleotides in length. According to another embodiment, the fragment of the nucleic acid molecule comprises the nucleotide sequence as set forth in SEQ ID NO:3 encoding the pro-hormone form of the insulin-like factor originated from the androgenic gland of *M. rosenbergii*, or a homolog thereof. According to a further embodiment, the fragment of the nucleic acid molecule comprises the nucleotide sequence as set forth in SEQ ID NO:4 encoding the mature B and A chains of the insulin-like factor originated from the androgenic gland of *M. rosenbergii*, or a homolog thereof.

According to another aspect, the present invention provides an insulin-like factor polypeptide originated from the androgenic gland of *M. rosenbergii* (designated herein Mr-IAG polypeptide) comprising the amino acid sequence as set forth in SEQ ID NO:5, or an analog or fragment thereof, wherein the analog has amino acid sequence identity of at least 70% to SEQ ID NO:5. According to some embodiments, the analog has amino acid sequence identity of at least 80%, 90%, 95%, or at least 99% to SEQ ID NO:5. According to a certain embodiment, the insulin-like factor polypeptide originated from the androgenic gland of *M rosenbergii* (Mr-IAG) comprises the amino acid sequence as set forth in SEQ ID NO:6, i.e., the amino acid sequence of mature B and A chains, or an analog or fragment thereof.

According to a further aspect, the present invention provides a double stranded RNA molecule that down regulates expression of an insulin-like factor gene of the androgenic gland of *M. rosenbergii* (Mr-IAG) comprising a sense strand and an antisense strand, the sense strand and the antisense strand together form a duplex, said antisense strand comprises a nucleotide sequence that is at least 70% complementary to the nucleotide sequence set forth in SEQ ID NO:1 or a homolog or fragment thereof.

According to some embodiments, the antisense strand comprises a nucleotide sequence that is at least 80%, alternatively at least 90%, 95%, or at least 99% complementary to SEQ ID NO:1 or a homolog or fragment thereof. In another embodiment, a fragment includes at least 21 bases. In another embodiment, a fragment or fragment thereof is a DNA fragment, a dsRNA fragment, or an antisense RNA fragment. According to an exemplary embodiment, the antisense strand comprises a nucleotide sequence that is 100% complementary to SEQ ID NO:1 or a fragment thereof.

According to additional embodiments, the antisense strand comprises a nucleotide sequence that is at least 70% complementary to the nucleotide sequence as set forth in SEQ ID NO:2 or a homolog or fragment thereof, wherein SEQ ID NO:2 is the open reading frame of Mr-IAG encoding the pre-pro-hormone form of the insulin-like factor originated from the androgenic gland of M. rosenbergii. According to further embodiments, the antisense strand comprises a nucleotide sequence that is at least 80%, alternatively at least 90%, further alternatively at least 95% or 99% complementary to SEQ ID NO:2 or a homolog or fragment thereof. According to a certain embodiment, the antisense strand consists of a nucleotide sequence that is 100% complementary to the open reading frame of Mr-IAG as set forth in SEQ ID NO:2. In another embodiment, the antisense strand comprises or consists the ribonucleic acid sequence of SEQ ID NO: 33 or 34. In another embodiment, the antisense strand comprises or consists a fragment (at least 20 BPs) of the ribonucleic acid sequence of SEQ ID NO: 33 or 34. In another embodiment, the antisense strand comprises or consists a ribonucleic acid sequence that is at least 70% identical or homologues to SEQ ID NO: 33 or 34. In another embodiment, the antisense strand comprises or consists a ribonucleic acid sequence that is at least 80% identical or homologues to SEQ ID NO: 33 or 34. In another embodiment, the antisense strand comprises or consists a ribonucleic acid sequence that is at least 90% identical or homologues to SEQ ID NO: 33 or 34. In another embodiment, the antisense strand comprises or consists a ribonucleic acid sequence that is at least 95% identical or homologues to SEQ ID NO: 33 or 34.

According to further embodiments, the antisense strand comprises a nucleotide sequence that is at least 70% complementary to the nucleotide sequence as set forth in SEQ ID NO:3 or a homolog or fragment thereof, wherein SEQ ID NO:3 encodes the pro-hormone form of the insulin-like factor secreted from the androgenic gland of M. rosenbergii.

According to further embodiments, the antisense strand comprises a nucleotide sequence that is at least 70% complementary to the nucleotide sequence as set forth in SEQ ID NO:4 or a homolog or fragment thereof, wherein SEQ ID NO:4 encodes the mature form of the insulin-like factor secreted from the androgenic gland of M. rosenbergii.

According to further embodiments, the sense strand comprises a nucleotide sequence having at least 70% sequence identity to the nucleotide sequence selected from the group consisting of SEQ ID NO:1 to SEQ ID NO:4. According to additional embodiments, the sense strand has at least 80%, alternatively at least 90%, 95%, or 99% sequence identity to SEQ ID NO:2. According to a certain embodiment, the sense strand consists of the nucleotide sequence as set forth in SEQ ID NO:2.

According to yet further embodiments, the sense strand and antisense strand each comprises from about 20 to about 2800 nucleotides in length. Alternatively, the sense strand and antisense strand each comprises from about 100 to about 700 nucleotides in length, further alternatively each strand comprises from about 200 to about 600 nucleotides, yet further alternatively each strand comprises from about 450 to about 520 nucleotides in length.

According to another aspect, the present invention provides a DNA construct for generating a double stranded RNA molecule capable of down regulating the expression of an insulin-like factor gene of the androgenic gland of M. rosenbergii (Mr-IAG), the DNA construct comprises a promoter operably linked to a nucleic acid molecule which is transcribed to an RNA molecule that forms a double stranded RNA, the nucleic acid molecule comprises:

a first nucleotide sequence having at least 70% sequence identity to SEQ ID NO:1 or a fragment thereof; and (ii) a second nucleotide sequence having at least 70% sequence identity to a complementary sequence of SEQ ID NO:1 or a fragment thereof, wherein the RNA molecule transcribed from the DNA construct down regulates the expression of the insulin-like factor gene.

According to some embodiments, the first and second nucleotide sequences within the DNA construct each comprises from about 20 nucleotides to about 2800 nucleotides in length, alternatively each nucleotide sequence comprises from about 100 to about 700 nucleotides, further alternatively each nucleotide sequence comprises from about 200 to about 600, or from about 450 to about 520 nucleotides in length.

According to additional embodiments, the first nucleotide sequence within the DNA construct has at least 80% sequence identity, or at least 90%, 95%, or at least 99% sequence identity to the nucleotide sequence set forth in SEQ ID NO:1 or a fragment thereof. According to a certain embodiment, the first nucleotide sequence has 100% sequence identity to the nucleotide sequence set forth in SEQ ID NO:1 or to a fragment thereof.

According to further embodiments, the first nucleotide sequence within the DNA construct has at least 70% sequence identity to the nucleotide sequence as set forth in any one of SEQ ID NO:2 to SEQ ID NO:4 or to a fragment thereof. According to other embodiments, the vector has at least 80%, 90%, 95%, or at least 99% sequence identity to the nucleotide sequence as set forth in any one of SEQ ID NO:2 to SEQ ID NO:4 or to a fragment thereof. According to a certain embodiment, the first nucleotide sequence within the DNA construct has 100% sequence identity to the nucleotide sequence as set forth in SEQ ID NO:2.

According to yet further embodiments, the second nucleotide sequence has at least 80%, 90%, 95%, or at least 99% sequence identity to a complementary sequence selected from the group consisting of SEQ ID NO:1 to SEQ ID NO:4, or to a fragment thereof.

According to further embodiments, the first and second nucleotide sequences are operably linked to the same promoter. Alternatively, the first nucleotide sequence is operably linked to a first promoter, and the second nucleotide sequence is operably linked to a second promoter.

According to a further aspect, the present invention provides a transgenic male decapod crustacean comprising at least one cell transfected with a double stranded RNA molecule that down regulates expression of an insulin-like factor gene according to the principles of the present invention. According to some embodiments, the transgenic male decapod crustacean is selected from the group consisting of M. rosenbergii, M. malcolmsonii, and Palaemon serratus. According to a certain embodiment, the transgenic male decapod crustacean is a male M. rosenbergii.

According to another aspect, the present invention provides a transgenic male decapod crustacean comprising at least one cell transfected with a DNA construct for generating a double stranded RNA (dsRNA) molecule, the dsRNA capable of down regulating the expression of an insulin-like factor gene according to the principles of the present invention. According to some embodiments, the transgenic male decapod crustacean is selected from the group consisting of *M. rosenbergii, M. malcolmsonii*, and *Palaemon serratus*. According to a certain embodiment, the transgenic male decapod crustacean is a male *M. rosenbergii*.

According to yet further aspect, the present invention provides a transgenic live-feed organism for feeding prawns, the live-feed organism is transfected with a double stranded RNA or a DNA construct according to the principles of the present invention.

According to still further aspect, the present invention provides a method for down-regulating the expression of an insulin-like factor gene of the androgenic gland in a male organism of the decapod crustacean order comprising introducing into at least one cell of the male organism of said decapod crustacean order a double stranded RNA molecule or a DNA construct according to the principles of the present invention.

According to some embodiments, introducing the double stranded RNA or the DNA construct is performed by injection, immersion, transdermal, or feeding. According to a certain embodiment, the double stranded RNA or DNA construct is administered by injection.

According to yet further aspect, the present invention provides a method for determining the gender of a decapod crustacean comprising the following steps: obtaining a sample of hemolymph of a decapod crustacean; and detecting the level of an insulin-like factor polypeptide comprising the amino acid sequence selected from the group consisting of SEQ ID NO:5 and SEQ ID NO:6 or an analog or fragment thereof, wherein the presence of the insulin-like factor polypeptide or an analog or fragment thereof indicates that the decapod crustacean is a male decapod crustacean. According to some embodiments, detecting the level of an insulin-like factor polypeptide or an analog or fragment thereof is performed by immunological methods. In another embodiment, gender determination is performed on the transcript level as well, removal of the 5$^{th}$ walking legs including the AGs, RNA extraction and RT-PCR.

According to a further aspect, the present invention provides a method for determining the gender of a decapod crustacean comprising the following steps: obtaining a sample of hemolymph of a decapod crustacean; and detecting the level of a polynucleotide encoding an insulin-like factor, the polynucleotide comprises the nucleotide sequence selected from the group consisting of SEQ ID NO:1 to SEQ ID NO:4 or a homolog or fragment thereof, wherein the presence of the polynucleotide encoding the insulin-like factor or a homolog or fragment thereof indicates that the decapod crustacean is a male decapod crustacean.

According to yet further aspect, the present invention provides an expression vector comprising a nucleic acid molecule as set forth in SEQ ID NO:1 or a homolog or fragment thereof, wherein the homolog has sequence identity of at least of 70% to SEQ ID NO:1. According to some embodiments, the homolog within the expression vector has sequence identity of at least 80% to SEQ ID NO:1, alternatively of at least 90%, 95%, or at least 99% sequence identity to SEQ ID NO:1. According to a certain embodiment, the expression vector comprises a nucleic acid molecule consisting of the nucleotide sequence selected from the group consisting of SEQ ID NO:2 to SEQ ID NO:4.

According to a further aspect, the present invention provides a composition comprising as an active ingredient an insulin-like factor polypeptide according to the principles of the present invention.

According to another aspect, the present invention provides a composition comprising as an active ingredient an expression vector comprising a nucleic acid molecule comprising a nucleotide sequence as set forth in SEQ ID NO:1 or a homolog or fragment thereof according to the principles of the present invention.

According to yet further aspect, the present invention provides a method for gaining a male decapod phenotype comprising administering to a decapod crustacean a composition comprising as an active ingredient: (i) an insulin-like factor polypeptide comprising the amino acid sequence as set forth in SEQ ID NO:5 or SEQ ID NO:6 or an active analog or fragment thereof; or (ii) an expression vector comprising a nucleic acid molecule comprising the nucleotide sequence selected from the group consisting of SEQ ID NO:1 to SEQ ID NO:4 or a homolog or fragment thereof according to the principles of the present invention, thereby increasing Mr-IAG polypeptide level in the decapod crustacean. According to one embodiment, the decapod crustacean is a male decapod crustacean. According to another embodiment, the decapod crustacean is a female decapod crustacean. According to a certain embodiment, the decapod crustacean is *M. rosenbergii*.

According to another aspect, the present invention provides an antibody directed to an insulin-like factor polypeptide of the androgenic gland of *M. rosenbergii* (Mr-IAG), the insulin-like factor polypeptide comprises an amino acid sequence selected from the group consisting of SEQ ID NO:5 and SEQ ID NO:6, or an analog or fragment thereof, wherein the analog has amino acid sequence identity of at least 70% to SEQ ID NO:5 or SEQ ID NO:6. According to a certain embodiment, the insulin-like factor polypeptide consists of the amino acid sequence as set forth in SEQ ID NO:6.

According to another aspect, the present invention provides a method of producing a decapod crustacean population having a majority of males, the method comprising the step of breeding a male decapod crustacean with a neofemale decapod crustacean. According to the principles of the present invention, the neofemale decapod crustacean is produced by down regulating expression of insulin-like factor gene of the androgenic gland (IAG) or by down regulating activity of insulin-like factor polypeptide (IAG).

According to some embodiments, down regulating the expression of IAG is obtained by administering to a male decapod crustacean a polynucleotide selected from the group consisting of a double stranded RNA that down regulates the expression of IAG, an antisense RNA, such as the antisense strand of SEQ ID NO: 33, that down regulates the expression of IAG, a DNA construct for generating a double stranded RNA capable of down regulating the expression of IAG, and a vector for generating a single stranded RNA capable of down regulating the expression of IAG.

According to additional embodiments, down regulating the activity of insulin-like factor polypeptide (IAG) is obtained by administering to a male decapod crustacean an agent selected from the group consisting of an inhibitor of IAG activity and an inhibitor of IAG binding.

According to further embodiments, the decapod crustacean is selected from the group consisting of *M. rosenbergii, M. malcolmsonii*, and *Palaemon serratus*. According to an exemplary embodiment, the decapod crustacean is *Macrobrachium rosenbergii* (MR).

According to further embodiments, the majority of males in the decapod crustacean population comprises at least 50% males, alternatively at least 60% males, at least 70%, 80%, 90% or further alternatively at least 95% males. According to a certain embodiment, the decapod crustacean population consists of 100% males, i.e., all-male population.

According to further embodiments, the method of producing the decapod crustacean population having a majority of males further comprises, prior to the step of breeding, a step of administering to a male decapod crustacean a double stranded RNA molecule or an antisense RNA molecule that down regulates the expression of insulin-like factor gene of the androgenic gland (IAG), thereby generating a decapod crustacean neofemale. The present invention encompasses administering to a male decapod crustacean a composition comprising a polynucleotide, such as the double stranded RNA molecule or an antisense RNA molecule, so as to generate the neofemale. In another embodiment, the terms generating, obtaining and producing are used interchangeably.

According to some embodiments, the double stranded RNA comprises a sense strand and an antisense strand (such as but not limited to SEQ ID NOs: 34 and 33, respectively). In another embodiment, the sense strand and the antisense strand together form a duplex, said antisense strand comprises a ribonucleotide sequence that is at least 70% complementary to the nucleotide sequence as set forth in SEQ ID NO:1 or a fragment thereof. In another embodiment a fragment thereof comprises or consists at least 20 consecutive ribonucleotides. According to further embodiments, the antisense strand comprises a nucleotide sequence that is at least 80%, 90%, 95%, or 99% complementary to the nucleotide sequence as set forth in SEQ ID NO:1 or a fragment thereof. According to a certain embodiment, the antisense strand consists of a nucleotide sequence that is 100% complementary to SEQ IED NO:1 or a fragment thereof. In another embodiment, SEQ ID NO: 1 comprises or consists:

According to additional embodiments, the antisense strand of the double stranded RNA comprises a nucleotide sequence that is at least 70% complementary to the nucleotide sequence set forth in SEQ ID NO:2 or a fragment thereof. According to yet further embodiments, the antisense strand comprises a nucleotide sequence that is at least 80%, 90%, 95% or 99% complementary to the nucleotide sequence set forth in SEQ ID NO:2 or a fragment thereof. In another embodiment, a fragment of the antisense molecule, sense molecule or dsRNA molecule comprises or consists at least 20 consecutive ribonucleotides. According to a certain embodiment, the antisense strand consists of a nucleotide sequence that is 100% complementary to SEQ IED NO:2 or a fragment thereof.

In another embodiment, a fragment of the antisense molecule, sense molecule or dsRNA molecule comprises or consists at least 20 consecutive ribonucleotides of any one of SEQ ID NOs: 1-4 and 33-34.

According to one embodiment, the antisense strand comprises or consists the following ribonucleotides sequence: CUGGAACUGCAGGUGUUAACGCCGGG ACGCAGCUCGAUGCAAUAUUCGGCGACUUCCUCGAAGUUGCAGCGUCUGAAAG AGGCGUUGUUGCAGCAUUCCUCCCUUGGACUUCUCCUCACGC UGUCCCUCCGG AAGCGACGCUUCGAAUGCAGCAUAUUGUUCGCUUCUUCCCUGCUCAGCGUCAU GUGCUGAAUCUCCUCCUCCACCUUAGAUACCUUCUGAGUUUCUUCGUCAGCCA UGGUCAAGUGGGUAGCUCUCGGGUGGGCGAGCGAUGGAGACUUCGUAGAAGG AACGGUAUAGAUGUCAGCA-GAUCGUCGCUCUUUGGAAACGUAGGUGGGUCCU GGGUUGAUGUAGUUGUUGUGUCUCAG-GCAGACGGAGGCAAGGGUGUUCGUUA UGUCGCCGCAGUCAAAGUCAACGGAGAGGCAUUC-GAUCUCAUAGCUCGAAGAA GGUUGAGGGAGAAGCGAUGCUAC-GAGUGAGCAGAACAACACACACUUGAUCU CGGCAUUCCAGUAUCCCAU (SEQ ID NO: 33). According to additional embodiments, the antisense strand of the double stranded RNA comprises a nucleotide sequence that is at least 70% identical or homologous to the nucleotide sequence set forth in SEQ ID NO: 33 or a fragment thereof. According to yet further embodiments, the antisense strand comprises a nucleotide sequence that is at least 80%, 90%, 95% or 99% identical or homologous to the nucleotide sequence set forth in SEQ ID NO:33 or a fragment thereof. In another embodiment, a fragment of the antisense molecule, comprises or consists at least 20 consecutive ribonucleotides of SEQ ID NO: 33.

According to one embodiment, the sense strand comprises or consists the following ribonucleotides sequence: AUGGGAUACU GGAAUGCCGA GAUCAAGUGU GUGUUGUUCUGCUCACUCGUAGCAUCGCUUCUCCCUCAACCUUCLTUCGAGCUA UGAGAUCGAAUGCCUCUCCGUUGACUUUGACUGCGGCGACAUAACGAACACCC UUGCCUCCGUCUGCCUGAGACACAACAACUACAUCAACCCAGGACCCACCUAC GUUUCCAAAGAGCGACGAUCUGCUGA-CAUCUAUACCGUUCCUUCUACGAAGUC UCCAUCGCUCGCCCACCCGAGAGCUACCCACUUGACCAUGGCUGACGAAGAAA CUCAGAAGGUAUCUAAGGUGGAGGAGGAGAUUCAGCACAUGACGCUGAGCAG GGAAGAAGCGAACAAUAUGCUGCAUUCGAAGCGUCGCUUCCGGAGGGACAGC GUGAGGAGAAGUCCAAGGGAGGAAAUGCUGCAACAACGCCUCUUUCAGACGCU GCAACUUCGAGGAAGUCGCCGAAUAUUGCAUCGAGCUGCGUCCCGGCGUUAAC ACCUGCAGUUCCAG (SEQ ID NO: 34). According to additional embodiments, the sense strand of the double stranded RNA comprises a nucleotide sequence that is at least 70% identical or homologous to the nucleotide sequence set forth in SEQ ID NO: 34 or a fragment thereof. According to yet further embodiments, the sense strand comprises a nucleotide sequence that is at least 80%, 90%, 95% or 99% identical or homologous to the nucleotide sequence set forth in SEQ ID NO:34 or a fragment thereof. In another embodiment, a fragment of the sense molecule, comprises or consists at least 20 consecutive ribonucleotides of SEQ ID NO: 34.

In another embodiment, a dsRNA molecule of the invention comprises a strand encoded by SEQ ID NO: 33 or a fragment thereof comprising at least 21 bases. In another embodiment, a dsRNA molecule of the invention comprises a strand encoded by SEQ ID NO: 34 or a fragment thereof comprising at least 21 bases. In another embodiment, a dsRNA molecule of the invention comprises strands encoded by SEQ ID NOs: 33 or 34 or fragments thereof comprising at least 21 bases.

According to further embodiments, the antisense strand comprises a nucleotide sequence that is at least 70% complementary to the nucleotide sequence set forth in SEQ ID NO:3 or a fragment thereof. According to yet further embodiments, the antisense strand comprises a nucleotide sequence that is at least 80%, 90%, 95%, or 99% complementary to the nucleotide sequence set forth in SEQ ID NO:3 or a fragment thereof. According to a certain embodiment, the antisense strand consists of a nucleotide sequence that is 100% complementary to SEQ IED NO:3 or a fragment thereof.

According to yet further embodiments, the antisense strand comprises a nucleotide sequence that is at least 70% complementary to the nucleotide sequence set forth in SEQ ID NO:4. According to yet further embodiments, the antisense strand comprises a nucleotide sequence that is at least 70%, 80%, 90%, 95% or 99% complementary to the nucleotide sequence set forth in SEQ ID NO:4. According to a certain embodiment, the antisense strand is 100% complementary to the nucleotide sequence set forth in SEQ ID NO:4. According to a certain embodiment, the antisense strand consists of a nucleotide sequence that is 100% complementary to SEQ IED NO:4 or a fragment thereof.

According to still further embodiments, the sense strand and antisense strand comprises from about 20 to about 800 nucleotides in length.

According to some embodiments, the step of administering the double stranded RNA molecule or an antisense RNA molecule (and thus converting a genetic male into a neofemale—a fully functional female with male sex chromosomes) is performed at an early stage of post larvae. According to further embodiments, the early stage of post larvae ranges from day 1 to about day 180 post larvae. According to certain embodiments, the step of administering the double stranded RNA molecule or an antisense RNA molecule is performed at about day 10 to day 50 post larvae, such as at about day 20 to day 30 post larvae. In another, embodiment, administration of the double stranded RNA molecule or antisense RNA molecule is performed in the larva.

According to another aspect, the present invention provides a decapod crustacean population having a majority of males, the decapod crustacean population obtained by a method comprising the step of breeding a male decapod crustacean with a neofemale decapod crustacean, wherein the neofemale decapod crustacean is genetically a male (sex chromosomes) that underwent IAG silencing or down regulation of the expression of IAG. In another embodiment, the neofemale decapod crustacean is genetically a male (sex chromosomes) that was treated with an agent such as an IAG antagonist that down regulated the activity of IAG polypeptide. In another embodiment, a neofemale is male (genetically) that underwent a procedure wherein the expression or activity of IAG were down-regulated. In another embodiment, a neofemale is genetically a male (male sex chromosomes) with a fully functional female reproductive system.

In another embodiment, down regulation of IAG expression or activity is performed until 180 days post-larva. In another embodiment, a neofemale of the invention is mated with a male upon sexual maturation of the neofemale (a fully developed female that is able to reproduce). According to an exemplary embodiment, the decapod crustacean is *Macrobrachium rosenbergii* (MR). According to some embodiments, a decapod crustacean population having a majority of males comprises at least 50% males, at least 60%, 70%, 80%, 90%, or 95% males. According to a certain embodiment, the decapod crustacean population consists of 100% males.

These and other embodiments of the present invention will be better understood in relation to the figures, description, examples and claims that follow.

BRIEF DESCRIPTION OF THE FIGURES

FIGS. 1A-1F show the effects of endocrine manipulation through bilateral removal of the XO-SG complex on *M. rosenbergii* male reproductive system. FIGS. 1A and 1B show the proximal part of the male reproductive system of intact and endocrinologically induced *M. rosenbergii* males, respectively; FIG. 1C, FIG. 1E and FIG. 1D, FIG. 1F show H & E staining of 5 μm cross-section of the terminal ampulae of intact males and endocrinologically induced males, respectively, shown in different magnitudes (X100 in FIGS. 1C and 1D; and X400 in FIGS. 1E and 1F). SD—Sperm Duct; GP—Gonopore; AG—Androgenic gland. Broken line denotes plain of section.

FIG. 2 shows the *M. rosenbergii* insulin like AG (Mr-IAG) cDNA sequence (SEQ ID NO:1) and deduced Mr-IAG protein (SEQ ID NO:3) according to the predicted open reading frame. The amino acid sequence of the putative signal peptide appears in bold letters, that of the putative B and A chains is underlined, that of the putative C peptide appears in italics, that of the predicted arginine C proteinase cleavage sites is boxed, and the stop codon is marked with an asterisk.

FIG. 3 shows the nucleotide sequence of the open reading frame of the Mr-IAG gene as set forth in SEQ ID NO:2.

FIGS. 4A-B show the alignment and comparison of Mr-IAG predicted B and A chains with other known AG crustacean insulin-like sequences. FIG. 4A, Sequence alignment of predicted mature AG specific factors from three decapods (*M. rosenbergii, C. quadricarinatus* and *C. destructor*) and mature AGHs from three isopods (*A. vulgare, P. scaber* and *P. dilatatus*). The conserved cysteine residues are marked by boxes and the two predicted inter-chain and one intra-chain disulfide bonds are linked. Non-conserved cysteine residues in Mr-IAG are boxed. Predicted N-glycosylation sites are circled. FIG. 4B, A phylogram of all the known crustacean AG insulin-like sequences with distances. Bar represents number of substitutions per site.

FIG. 5A, RT-PCR products using Mr-IAG (top) and of Mar-SRR (middle) primers to amplify cDNA from different male tissues. RNA from the AG (top and bottom), and from sperm duct (middle) was used as negative control. *M. rosenbergii* β-actin (bottom) was used as a positive control. FIG. 5B, Northern blot analysis using Mr-IAG probe (top). Each lane was loaded with 5 μg total RNA as indicated by the rRNA bands (bottom).

FIG. 6A, RT-PCR products using Mr-IAG (top), and ft-actin (bottom) specific primers to amplify cDNA derived from a pair of sexually mature males from each of the three different morphotypes AG—androgenic gland. SD—sperm duct. FIG. 6B, The Mr-IAG relative transcript level in the different morphotypes. Bars represent standard deviation. FIG. 6C, Mr-IAG in situ hybridization in different *M. rosenbergii* males morphotypes. Left to right: Haematoxylin & Eosin stain (H&E), sense and anti-sense probes hybridized with Mr-IAG in situ, in the three male morphotypes (top to bottom): blue claw (BC), orange claw (OC) and small males (SM). H&E and anti-sense are also shown at higher magnification (×400, boxed areas).

FIG. 8A, Cumulative molt events of vehicle-injected (○) and Mr-IAG-dsRNA-injected (●) groups in the in vivo assay: Molted individuals are represented as a percentage of each group. The end of the repeated-injection period is marked as—✻— (day 55). Statistically significant differences are indicated with asterisks, p<0.001. FIG. 8B, Cumulative molt increment of vehicle-injected (☐) and Mr-IAG-dsRNA-injected (■) groups during three molt events: cumulative molt increment is expressed by 100× weight after molt/weight at start of experiment. Bars represent SEM, Asterisk represents the statistically significant difference observed at the third molt event.

FIGS. 10A-F show dorsoventral H&E stained sections in Mr-IAG silenced and control males. Dorsoventral sections of the fifth walking leg base (FIGS. 10A-D) and the cephalothorax (FIGS. 10E-F) of representative individuals from the Mr-IAG-dsRNA-injected group (FIGS. 10A, 10C, 10E) and the vehicle-injected group (FIGS. 10B, 10D, 10F). Cross-sections of the terminal ampula region of the empty sperm duct (SD) shows hyperplasic and hypertrophied AG cells in an individual from the Mr-IAG-dsRNA-injected group (FIGS. 10A and 10C), vis-à-vis the spermatozoa-filled sperm duct with normal AG cells in a vehicle-injected individual (FIGS. 10B and 10D). Dorsal sections showing inactive testis lobules (TS) in an individual of the Mr-IAG-dsRNA-injected group (FIG. 10E), vis-à-vis the active testis lobules in the vehicle-injected individual (FIG. 10F), containing both spermatogonia (SG) and spermatozoa (SG).

FIGS. 11A-I show that Mr-IAG silencing induces anatomical sex reversal. Longitudinal sections obtained from control male (A-C), Mr-IAG-silenced male (D-F) and control female (G-I) individuals. Hep—Hepatopancreas; Ooc—Oocytes; Oog—Oogonia; Ovd—Oviduct; Sg—Spermatogonia; Sz—Spermatozoa; Tes—Testes; Pvd—Proximal Vas deferens; Dvd—Distal vas deferens; WL—Walking leg.

FIGS. 12A-B show that Mr-IAG-silenced neo-female produces all-male progeny. FIG. 12A shows developed ovaries (seen from dorsal view in upper panel, arrow) in a genetic male in which Mr-IAG was silenced. Later, when mated with a normal male, the modified individual laid and incubated eggs in the brood-chamber (ventral view in bottom panel, arrow, with a few eggs magnified). FIG. 12B. Upper panel—Agarose gel of PCR products generated from intact male control individual, intact female control individual as well as from a control female and individuals from its progeny as a template. Lower panel—Agarose gel of PCR products generated from intact male control individual, intact female control individual as well as from a neo-female and individuals from its progeny. n.c.—negative control, p.c.—positive control, fs.—female-specific marker.

FIG. 14A shows relative Mr-IAG transcript levels quantified by real-time RT-PCR performed 3 days, 1 week or 2 weeks after injection of Mr-IAG dsRNA. FIG. 14B shows relative Mr-IAG transcript levels quantified by real-time RT-PCR performed 1 week after injection of 5, 1 or 0.1 µg of Mr-IAG dsRNA/g body weight. Asterisks represent significant difference (>0.005) and error bars represent SEM.

DETAILED DESCRIPTION OF THE INVENTION

Figure 5A:
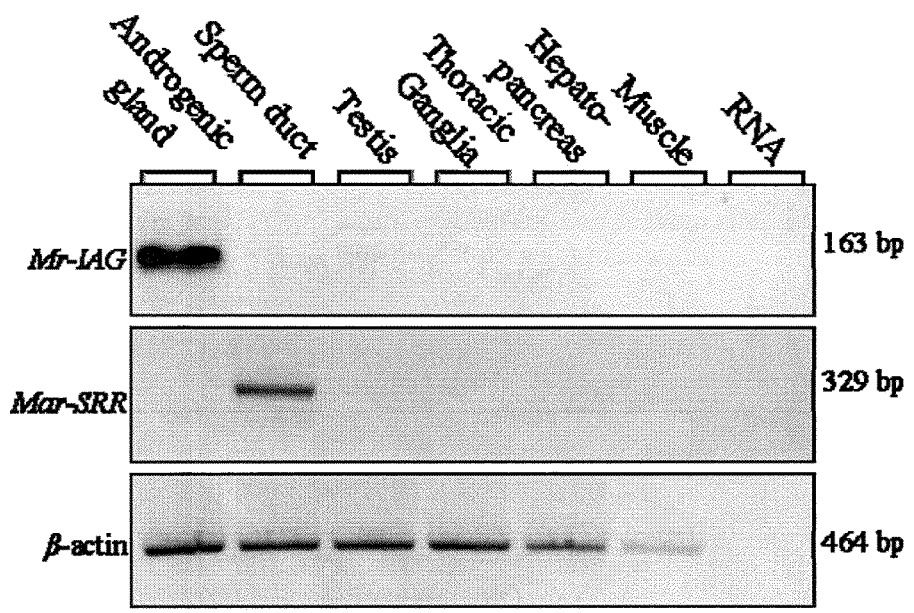
FIGS. 5A-B show tissue specific expression of Mr-IAG in *M. rosenbergii* male.

The present invention provides a cDNA sequence of an insulin-like factor originated in and secreted from the androgenic gland of *M. rosenbergii* termed Mr-IAG and the deduced amino acid sequence encoded by this cDNA. The present invention further provides methods for silencing the Mr-IAG gene expression, particularly by RNA interference.

Typically, RNA interference (RNAi) refers to the process of sequence-specific post transcriptional gene silencing mediated by small interfering RNAs (siRNA). Long double stranded RNA (dsRNA) in cells typically stimulates the activity of a ribonuclease III enzyme referred to as dicer. Dicer is involved in the processing of the long dsRNA into short pieces of siRNA. siRNAs derived from dicer activity are typically about 21-23 nucleotides in length and include duplexes of about 19 base pairs.

The RNAi response also features an endonuclease complex containing a siRNA, commonly referred to as an RNA-induced silencing complex (RISC), which mediates cleavage of single stranded RNA having sequence complementary to the antisense strand of the siRNA duplex. Cleavage of the target RNA takes place in the middle of the region complementary to the antisense strand of the siRNA duplex. Without being bound to any mechanism of processing or action, the present invention relates to double stranded RNAs or antisense RNA molecules, whether processed or not, as a tool for down regulating gene expression.

Gene expression can also be down regulated by microRNAs, single-stranded RNA molecules of about 21-23 nucleotides in length, encoded by genes that are transcribed from DNA but not translated into protein. MicroRNAs base pair with their complementary mRNA molecules and induce mRNA degradation in the RISC complex.

Gene expression can further be down regulated by an antisense oligonucleotide complementary to a region of an mRNA wherein the antisense oligonucleotide is capable of specifically hybridizing with the region of the mRNA, thereby inhibiting the expression of a gene. Thus, the present invention encompasses double stranded RNAs, micro RNAs, antisense oligonucleotides, short hairpin RNAs (shRNAs), each capable of down regulating the expression of an insulin-like factor of the androgenic gland of decapod crustaceans, particularly of *M. rosenbergii*.

The practice of the present invention will employ, unless otherwise indicated, conventional methods of microbiology, molecular biology and recombinant DNA techniques within the skill of the art. Such techniques are explained fully in the literature. See, e.g., Sambrook, et al. Molecular Cloning: A Laboratory Manual (Current Edition); DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition);

DEFINITIONS

The term "nucleic acid" refers to deoxyribonucleotides or ribonucleotides and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides, conservatively modified variants thereof, complementary sequences, and degenerate codon substitutions that have similar binding properties as the reference nucleic acid and are metabolized in a manner similar to naturally occurring nucleotides. The terms "nucleic acid" or "polynucleotide" are used interchangeably. In another, embodiment, a nucleic acid is an isolated nucleic acid. In another, embodiment, a nucleic acid of the present invention does not exist naturally and therefore is not in an isolated form.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The term "gene delivery" or "gene transfer" refers to methods or systems for reliably inserting foreign nucleic acids into target cells. Such methods can result in transient or long term expression of genes.

The term "DNA construct" or "expression vector" refers to any agent such as a plasmid, cosmid, virus, autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner. Such DNA constructs or vectors are capable of introducing a 5' regulatory sequence or promoter region and a DNA sequence for a selected gene product into a cell in such a manner that the DNA sequence is transcribed into a functional mRNA which is translated and therefore expressed. DNA constructs or expression vectors may be constructed to be capable of expressing double stranded RNAs or antisense RNAs in order to inhibit translation of a specific RNA of interest.

The term "operatively linked" means that a selected nucleic acid sequence is in proximity with a promoter to allow the promoter to regulate expression of the selected nucleic acid sequence. In general, the promoter is located upstream of the selected nucleic acid sequence in terms of the direction of transcription and translation.

The term "homolog" of a nucleic acid molecule is a sequence that is substantially similar to the sequence of the native molecule. For nucleotide sequences, homologs include those sequences that, because of the degeneracy of the genetic code, encode the identical amino acid sequence of the native protein. Naturally occurring allelic homologs such as these can be identified with the use of molecular biology techniques, as, for example, with polymerase chain reaction (PCR) and hybridization techniques. Homolog nucleotide sequences also include synthetically derived nucleotide sequences, such as those generated, for example, by using site-directed mutagenesis, which encode the native polypeptide, as well as those that encode a polypeptide having amino acid substitutions, deletions or additions. Generally, nucleotide sequence homologs of the invention will have at least about 70%, 80%, 90%, 95%, 96%, 97%, 98%, 99%, or 100% sequence identity to the native (endogenous) nucleotide sequence.

The term "hybridization" refers to the ability of a strand of nucleic acid to join with a complementary strand via base pairing. Hybridization occurs when complementary sequences in the two nucleic acid strands bind to one another.

The term "homology" when used in relation to nucleic acid sequences refers to a degree of similarity or identity between at least two nucleotide sequences. There may be partial homology or complete homology (i.e., identity). "Sequence identity" refers to a measure of relatedness between two or more nucleotide sequences, expressed as a percentage with reference to the total comparison length. The identity calculation takes into account those nucleotide residues that are identical and in the same relative positions in their respective sequences. A gap, i.e. a position in an alignment where a residue is present in one sequence but not in the other is regarded as a position with non-identical residues. A widely used and accepted computer program for performing sequence alignments is CLUSTALW v1.6 (Thompson, et al. Nucl. Acids Res., 22: 4673-4680, 1994). Similarly, the term "homology" when used in relation to protein sequences refers to a degree of similarity or identity between at least two protein sequences. There may be partial homology or complete homology (i.e., identity). It is to be appreciated that the cysteine backbone should be fully conserved in the nucleic acid sequence (DNA, cDNA, mRNA, and the like) encoding the insulin-like factor polypeptide as well as in the insulin-like factor polypeptide as the cysteine backbone dictates the 3-D structure of the mature A and B chains of the insulin-like factor polypeptide.

The term "complementary" refers to the ability of polynucleotides to form base pairs with one another. Base pairs are typically formed by hydrogen bonds between nucleotide units in antiparallel polynucleotide strands. Complementary polynucleotide strands can base pair in the Watson-Crick manner (e.g., A to T, A to U, C to G), or in any other manner that allows for the formation of duplexes. As persons skilled in the art are aware, when using RNA as opposed to DNA, uracil rather than thymine is the base that is considered to be complementary to adenosine. However, when a U is denoted in the context of the present invention, the ability to substitute a T is implied, unless otherwise stated.

The phrase "duplex" refers to a structure consisting of two complementary or substantially complementary polynucleotides that form base pairs with one another, either by Watson-Crick base pairing or any other manner that allows for a stabilized duplex between polynucleotide strands that are complementary or substantially complementary. For example, a polynucleotide strand having 21 nucleotides can base pair with another polynucleotide of 21 nucleotides, yet only 19 bases on each strand are complementary or substantially complementary, such that the "duplex" has 19 base pairs. The remaining bases may, for example, exist as 5' and 3' overhangs. Further, within the duplex region, 100% complementarity is not required; substantial complementarity is allowable within a duplex region. Substantial complementarity refers to at least 70% or greater complementarity.

The term "transfection" is used to refer to the uptake of exogenous or foreign nucleic acids by a cell. A cell has been "transfected" when an exogenous nucleic acid has been introduced inside the cell. Transfection can be used to introduce one or more exogenous nucleic acid moieties, such as a double stranded RNA, DNA construct, and other nucleic acid molecules, into suitable cells. The term refers to uptake of the genetic material.

The term "transgenic" when used in reference to a decapod or live-feed organism refers to a decapod or live-feed organism that has been administered or transfected with at least one exogenous nucleic acid in one or more of its cells.

The term "neofemale" refers to a genotypic decapod crustacean male that contains one or more female sexual characteristics such as ovaries and oviduct and is able to reproduce similarly or equivalently to a female. The neofemale is essentially devoid of male sexual characteristics such as appendix masculine, testes, sperm ducts and spermatogenesis. The neofemale is produced by down regulating the expression of the insulin-like factor gene of the androgenic gland (IAG) and/or by down regulating the expression of insulin-like factor polypeptide (IAG) by the methods of the present invention.

The term "expression" with respect to a gene sequence refers to transcription of the gene and, as appropriate, translation of the resulting mRNA transcript to a protein. Thus, as will be clear from the context, expression of a protein coding sequence results from transcription and translation of the coding sequence.

The term "down regulated," as it refers to genes inhibited by the subject RNAi method, refers to a diminishment in the level of expression of a gene(s) in the presence of one or more single or double stranded RNA(s) or DNA construct(s) when compared to the level in the absence of such single or double stranded RNA(s) or DNA construct(s). The term "down regulated" is used herein to indicate that the target gene expression is lowered by 1-100%. For example, the expression may be reduced by about 10, 20, 30, 40, 50, 60, 70, 80, 90, 95, or 99%. The term "down regulated" as it refers to IAG activity means reduction in insulin-like factor polypeptide activity in the presence of agents that inhibit IAG activity or inhibit the binding of IAG to its specific receptors.

The sequence of the double stranded RNA can correspond to the full length target gene, or a subsequence thereof. Double stranded RNA is "targeted" to a gene in that the nucleotide sequence of the duplex portion of the double stranded RNA is substantially complementary to a nucleotide sequence of the target gene. The double stranded RNA of the invention may be of varying lengths. The length of each strand of the double stranded RNA or a fragment thereof is preferably from about 20 to about 800 nucleotides; alternatively from about 100 to about 700 nucleotides, further alternatively from about 200 to 600 nucleotides, still alternatively from about 450 to about 520 nucleotides. However, an RNA strand of about 12 to about 20 nucleotides is also encompassed in the present invention. The term "about" refers to indicate that 10% above or below of the indicated value, e.g., number of nucleotides, are within the scope of the invention. The term "stably interact" refers to interaction of an RNA strand with a target nucleic acid (e.g., by forming hydrogen bonds with complementary nucleotides in the target gene under physiological conditions).

The open reading frame (ORF) or "coding region," which is known in the art to refer to the region between the translation initiation codon and the translation termination codon, is a preferred region which may be targeted effectively by siRNA. Other target regions include the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene), and the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene).

The double stranded RNA may be encoded by a DNA construct, and the DNA construct can also include a promoter. The DNA construct can also include a polyadenylation signal. In some embodiments, the polyadenylation signal is a synthetic minimal polyadenylation signal. The RNA duplex may be constructed in vitro using synthetic oligonucleotides.

The term "analog" as used herein refers to a polypeptide comprising altered sequences of an insulin-like factor derived from the androgenic gland of *M. rosenbergii* as set forth in SEQ ID NO:5 by amino acid substitutions, additions, or chemical modifications. By using "amino acid substitutions", it is meant that functionally equivalent amino acid residues are substituted for residues within the sequence resulting in a silent change. For example, one or more amino acid residues within the sequence can be substituted by another amino acid of a similar polarity, which acts as a functional equivalent, resulting in a silent alteration. Such substitutions are known as conservative substitutions. Additionally, a non-conservative substitution may be made in an amino acid so long as the activity of the analog in to cause male phenotypic sex differentiation is preserved if compared to the activity of the native Mr-IAG. The amino acid sequence of an analog according to the present invention has at least 70%, alternatively at least 80%, 90%, 95% or 99% identity to the amino acid sequence of the preprohormone form of the native insulin-like factor as set forth in SEQ ID NO:5 or to a fragment thereof, such as the amino acid sequence of the mature B and A chains as set forth in SEQ ID NO:6.

The term "fragment" refers to a polynucleotide or polypeptide which is a portion of a full length nucleic acid molecule or a full length polypeptide, respectively.

The present invention provides nucleic acids and polypeptides as listed in Table 1.

TABLE 1

| SEQ ID NO: | Sequence | |
|---|---|---|
| 1 | Nucleic acid | Full length cDNA encoding insulin-like factor of *M. rosenbergii* (Mr-IAG; data bank accession number FJ409645) |
| 2 | Nucleic acid | Open reading frame encoding the preprohormone form of Mr-IAG |
| 3 | Nucleic acid | cDNA encoding the prohormone form of Mr-IAG |
| 4 | Nucleic acid | cDNA encoding the mature form of Mr-IAG |
| 5 | Polypeptide | Preprohormone of Mr-IAG (data bank accession number ACJ38227) |
| 6 | Polypeptide | Mature form of Mr-IAG |

The term "pre-pro-hormone" form refers to an insulin-like factor polypeptide consisting of the signal peptide, B and A chains, the C peptide and the arginine C proteinase cleavage sites.

The term "pro-hormone" form refers to an insulin-like factor polypeptide consisting of the B and A chains, the C peptide and the arginine C proteinase cleavage sites.

The term "mature" form refers to an insulin-like factor polypeptide consisting of the B and A chains.

In accordance with the present invention, double stranded RNA specific to Mr-IAG mRNA was used to down-regulate the expression of the Mr-IAG gene.

RNA silencing can be induced by synthesizing double stranded RNA (dsRNA) molecules in vitro and transfecting these molecules into living host cells. In vitro synthesis methods include chemical synthesis and in vitro transcription methods, which are well known in the art. "Isolated" dsRNA refers to a dsRNA molecule that has been prepared in vitro. In vitro transcription can rely on the RNA polymerases of phages T7, T3 or SP6, for instance. RNA prepared in this way can be purified prior to being introduced into a target organism, for instance by extraction with a solvent or resin, precipitation, electrophoresis, chromatography, or a combination thereof. The RNA can be dried for storage or dissolved in an aqueous solution. Following RNA preparation, duplex formation can be initiated in vitro before the double stranded RNA is introduced into the target organism, such as by annealing through heating and subsequent cooling. The sense and antisense strands can be covalently cross-linked. Alternatively, complementary sense and antisense strands can be introduced separately or together into the target organism, allowing hybridization to occur in vivo.

Alternatively, double-stranded RNA molecules can be synthesized in vivo in host cells by transcription from a vector template or a DNA construct. In accordance with one embodiment of the invention, double stranded RNA is administered to aquatic organisms by means of a vector or a DNA construct which is capable of transcribing double stranded RNAs in vivo. Expression vectors can be constructed by techniques well known in the art and referred to, for instance, in Sambrook et al., ibid.

Such vectors are preferably plasmid DNA vectors or (retro-) viral vectors, which are relatively stable and therefore capable of being administered to aquatic organisms by a variety of routes, such as immersion in water, or in feed. Preferably the vector can be replicated in prokaryotic cells. If sustained effects are desired, the vector may be designed to replicate in eukaryotic cells. RNA is transcribed in vivo within the target cell from a vector equipped with appropriate transcription regulatory elements, including a suitable promoter and optionally terminator, enhancer or silencer sequences. The vectors of the invention can remain episomal (extrachromosomal) or become chromosomally integrated, for example by incorporating retroviral long-terminal repeat (LTR) sequences and a sequence encoding the corresponding retroviral integrase.

The dsRNA coding sequence (s) within the DNA construct is operatively linked to a promoter. The promoter may be constitutive or inducible. It may be an RNA polymerase II or RNA polymerase III promoter. The promoter may be selected to be one which functions in a wide variety of eukaryotic cells, such as the CMV promoter. Alternatively it may be a promoter sequence specific to the aquatic organism, for instance, heat shock or actin promoters. The vector or DNA construct may or may not incorporate other transcriptional regulatory elements such as enhancers, termination sequences, polyadenylation sequences (such as the BGH polyadenylation signal), and so on. Preferably, the dsRNA encoded by the vector is incapable of being translated into protein in prokaryotic or eukaryotic cells (e.g. the dsRNA lacks an IRES sequence and/or a start codon and/or a Shine-Dalgarno sequence, and/or is not polyadenylated and/or is too short to be translated).

If desired, the DNA vector may carry a reporter or marker gene which enables cells, tissues or organisms which have been successfully transfected to be identified. Examples of such marker genes are green fluorescent protein (GFP), firefly luciferase, and beta-galactosidase. Transfection can also be verified by techniques such as PCR and Southern blot hybridization.

A vector can be designed to achieve transcription of double stranded RNA in vivo in a target cell in a multitude of ways. In one type of construct the DNA sequence to be transcribed is flanked by two promoters, one controlling transcription of one of the strands, and the other that of the complementary strand. These two promoters may be the same or different. In vivo, the complementary RNA strands anneal to create dsRNA molecules. In another type of construct, vectors may be engineered to express from a single vector cassette a small, stem-loop or hairpin RNA (shRNA) which is processed in vivo to siRNAs. One side of the stem encodes a sequence, preferably of at least 18 nucleotides, which is complementary to a portion of a target RNA, and the other side of the stem is sufficiently complementary to the first side of the stem to hybridize with the first side to form a duplex stem. The intervening loop portion is preferably 4, 7, 11 or more nucleotides in length. The duplex stem may include the preferred 21-23 nucleotide sequences of the siRNA desired to be produced in vivo.

Alternatively an expression vector may incorporate two separate promoters, each of which directs transcription of either the sense or the antisense strand of a dsRNA (such as but not limited to SEQ ID NOs: 34 and 33, respectively). These two promoters may be of the same type or may be different. In vivo, the complementary RNA strands anneal to create dsRNA molecules. It is also possible for the sense and antisense strands of the dsRNA to be encoded by separate vectors, which are co-transfected into the target organism According to the present invention, an "RNA interference agent" or "RNAi agent" is either a double stranded RNA or a DNA construct engineered to be capable of transcribing a double stranded RNA within a target cell, which double stranded RNA comprises an RNA strand which is at least 70% complementary to the nucleotide sequence of SEQ ID NO:1 or to a homolog or fragment or portion thereof.

It is to be understood that the dsRNAs of the invention may be subject to chemical modifications (see, for example, US 2005/0080032 incorporated by reference as if fully set forth herein). Specific examples of modified dsRNA compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides. Additionally, modified oligonucleotides, according to the invention, may also contain one or more substituted sugar moieties.

Additionally, the oligonucleotides of the invention may be chemically linked to one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes.

RNAi agents can be administered to the target aquatic organisms of the invention by techniques including, but not limited to, electroporation, injection, microinjection, jet injection, immersion, ingestion (feeding), calcium phosphate-DNA co-precipitation, DEAE-dextran-mediated transfection, polybrene-mediated transfection, liposome fusion, lipofection, protoplast fusion, retroviral infection, and biolistics (particle bombardment, e.g. using a gene gun). Viral vectors transfect cells directly. For decapod crustaceans, injection, oral administration via immersion or feeding, or transdermal approach are preferred. The RNAi agent can be introduced into the target organism in a naked form. By "naked" is meant the RNAi agent is free from any delivery vehicle that can act to facilitate entry into the target cell, such as liposomal formulations, charged lipids, or precipitating agents. If preferred, a delivery agent may be used. The RNAi agent may be delivered in a composition which further comprises a nucleic acid condensing agent such as spermidine, protamine sulphate, poly-lysine, or others as known in the art.

An RNAi agent can be administered to a decapod crustacean at any stage in the lifecycle, including to unfertilized or fertilized eggs, or embryos, to the immature or larval phases, or to the mature phases. For practical reasons, if the RNAi agent is to be delivered by injection or microinjection to an animal, it is preferred if the animal is visible to the naked eye. In the case of *M. rosenbergii* it is most beneficial to administer the RNAi agent prior to or during, embryonic stages, larval stages or post larval (PL) stages, such as at 1-200 days of the post larval stages, preferably at 10-50 days of post larval stages.

In one approach in a method of administering an RNAi agent to a target organism, a live-feed organism carrying an RNAi agent is used. For instance, shrimp and prawns consume single-celled and multicellular food sources such as plankton, plankton-like filter feeders, algae, and yeast. These food sources can also be employed in aquaculture. It may be desired to transform these food sources with an RNAi agent in order that the target organism ultimately receives the RNAi agent by ingesting the food source (see, for example, US 2005/0080032, the content of which is incorporated by reference as if fully set forth herein). Artemia, Spirulina, Daphnia, Gammarus, Rotifera, bloodworms and tubifex worms are example of live feed sources used to nourish farmed shrimp and prawns, and which can be genetically engineered to deliver RNAi to the prawns. A live-feed organism is not necessarily alive when administered to the target organism. For example, live-feed organisms may be prepared in freeze-dried or frozen form.

The invention provides a composition comprising an RNAi agent comprising, or capable of directing transcription of, a dsRNA in which one strand or a subsequence thereof is at least 70% complementary to SEQ ID NO:1.

The composition of the invention may be in a solid, semi-solid, or liquid form. Depending on the mode of administration and on the nature of the RNAi agent, the compositions may be formulated appropriately for delivery to the target organism. The composition may further comprise a carrier. Carriers with which the RNAi agent can be admixed include conventional excipients, and may be for example, aqueous solvents such as water, saline or PBS, oil, dextrose, glycerol, wetting or emulsifying agents, bulking agents, stabilizers, anti-oxidants, preservatives, coatings, binders, fillers, disintegrants, diluents, lubricants, pH buffering agents, and the like.

For transmucosal or transdermal administration, penetrants appropriate to the barrier to be permeated are used in the formulation. Such penetrants are generally known in the art, and include, for example, detergents, bile salts, and fusidic derivatives. The dsRNA formulations of the present invention include, but are not limited to, solutions, emulsions, foams and liposome-containing formulations (see, for example, US 2005/0080032, incorporated by reference as if fully set forth herein).

Where the RNAi agent is dsRNA, care should be taken to ensure that the carrier or excipient is sterile and RNase free. In one embodiment the dsRNA is administered in conjunction with an RNase inhibitor (such as RNasin). The preferred amount of the RNase inhibitor per unit dose is from about 4 to 4000 units, usually from about 400 to 4000 units and more usually from about 400 to 1500 units. In addition or as an alternative, competitor RNA may be provided in the compositions of the invention, to serve as a competitive inhibitor of RNase activity. The precise sequence of the competitor RNA is irrelevant to its competitor activity, but it should be provided in excess over the amount of RNAi agent in the composition.

In one aspect, the invention encompasses the use of an RNAi agent in the manufacture of a composition for inhibiting the expression of IAG in decapod crustaceans and in particular Palaemonidae including, but not limited to, *Macrobrachium rosenbergii, Macrobrachium malcolmsonii*, and *Palaemon serratus*.

The compositions of the invention comprise an amount of the RNAi agent capable of reducing the amount of a target RNA by at least 30%, at times preferably by 40, 50, 60, 70, 80, or 90% or higher. Exemplary doses include milligram, microgram, or nanogram amounts of the agent per gram of an animal. The optimum dose varies according to the route of administration, but can be determined by the skilled person without undue burden. Similarly the frequency and timing of administration of the RNAi agent can best be determined by simple experimentation.

Additionally, the dsRNA compositions of the invention may contain more than one dsRNA compound, e.g., a first dsRNA targeted to a first nucleic acid and one or more additional dsRNA compounds targeted to a second nucleic acid target.

According to yet further embodiment, the present invention provides an antisense oligonucleotide sequence complementary to the nucleotide sequence as set forth in SEQ ID NO:1 or a homolog or fragment thereof, wherein the antisense oligonucleotide sequence is capable of specifically hybridizing with SEQ ID NO:1 or a homolog or fragment thereof, thereby inhibiting expression of an insulin-like factor of *M. rosenbergii*.

According to some embodiments, the region of the nucleotide sequence is selected from the group consisting of a 5'-untranslated region, coding region, stop codon region, and a 3'-untranslated region. According to certain embodiments, the antisense oligonucleotide sequence comprises at least 20 nucleotides. It is to be appreciated that the oligonucleotide sequence can consist of up to 500 nucleotides in length.

According to further embodiments, the antisense oligonucleotide sequence comprises at least one modified internucleoside linkage. Alternatively, the oligonucleotide sequence comprises at least one modified sugar. Preferably, the oligonucleotide sequence is linked to a promoter, wherein the promoter is operably linked to the antisense oligonucleotide sequence.

Example 1

Identification of Mr-IAG Gene and Polypeptide

Animals

Mature *M. rosenbergii* males (18-80 g) were collected from a breeding population that was hatched and grown at the Ben-Gurion University. Their morphotypes were determined by cheliped shape, coloration, spination and size in relation to carapace length. Endocrine manipulation was employed by X organ-Sinus gland complex (XO-SG) removal through bilateral eye-stalk ablation, causing hypertrophy of the AG (hAG) as described previously for *C. quadricarinatus* and also for *Macrobrachium nipponense*. The procedure was performed on 15 blue claw males and on orange claw and small males.

Juveniles, 110-120 days post-larvae ($PL_{110-120}$) were sexed according to the presence of genital papillae and appendix masculine.

Construction of a cDNA Library of the AG Using Suppression Subtractive Hybridization (SSH)

Total RNA isolation, cDNA preparation and subtraction library of the AG was done as described in Manor et al. (ibid.) using the cDNA from 30 hypertrophied AGs (hAGs) as the tester and the cDNA from other peripheral glands (a mix of mandibular and Y-organs) as the driver. After two hybridization cycles, unhybridized cDNAs, representing genes that are expressed in the AG but are absent in the driver, were amplified by two PCRs. The primary (24 cycles) and secondary (20 cycles) PCRs were performed as recommended in the Fermentas DNA polymerase manual and the PCR products were cloned into the pGEM-T easy vector (Promega) electroporatically transformed into competent bacteria. Clones containing the inserts were isolated and grown overnight. Plasmid DNA was purified (Qiagen Miniprep kit) and the inserts were sequenced.

Complete Sequence of M. rosenbergii-IAG Gene

The complete M. rosenbergii-MG (Mr-IAG) sequence was obtained by 3' and 5' rapid amplification of cDNA ends, carried out with the Clontech SMART™ RACE kit (BD Biosciences) according to the manufacturer's protocol. PCR was performed using the gene-specific forward primer 5'-GAGCAGGGAAGAAGCGAACAATATGCTG-3' (nt 628-655; SEQ ID NO:7) and reverse primer from the kit for the 3' RACE, the gene-specific reverse primer 5'-ATCATC-CCGTCCCTGTCCTATACTTGAC-3' (nt 821-848; SEQ ID NO:8) and the UPM (Universal Primers Mix) provided in the kit for the 5' RACE. The PCR products were cloned and sequenced as described above.

Bioinformatic Analyses

To enhance the quality of the selected expressed sequence tags (ESTs), the obtained cDNA sequences were first stripped of low quality, vector and primer sequences using Sequencher™ software (GeneCodes Corp.), followed by clustering and assembly. The resulting contigs and singlets were unified and their sequences were compared to the Uniprot database (Swiss-Prot+TrEMBL from 18.5.05), using a local installation of NCBI's BLASTx algorithm. The full length of one of the cDNA sequences, Mr-IAG, was computationally translated using the ExPASy Proteomics Server (http://ca.expasy.org/tools/dna.html) and the most likely frame was selected (5'43 3' Frame 2). The deduced amino acid sequence was further assessed by SMART (http://smart.embl-heidelberg.de/smart) and CBS Prediction Servers (http://www.cbs.dtu.dk/services). Multiple sequence alignment of the predicted Mr-IAG B and A chain sequences with the B and A chain sequences of the three AGHs known in Isopoda (Ohira et al., and Okuno et al., ibid), and with Cq-IAG (Manor et al., ibid) was performed using ClustalW. A phylogram of the five Crustacean insulin-like mature sequences was created with random number generator seed of 111, and 1000 bootstrap trials using ClustalX and viewed by TreeView.

RT-PCR

Complementary DNA was prepared by a reverse transcriptase reaction containing 1 µg of total RNA, extracted from mature males (AG, hAG, sperm duct, testis, peripheral glands, muscle, hepatopancreas, and thoracic ganglia), and M-MLV reverse transcriptase H minus (Promega) according to the manufacturer's instructions. The cDNA was then amplified by PCR as previously described by Manor et al. (ibid.) using four specific primers designed on the basis of the analyzed Mr-IAG sequence. Mr-IAG tissue specific expression was demonstrated by using forward (5'-GACAGCGT-GAGGAGAAGTCC-3' SEQ ID NO:9, nt 680-699) and reverse (5'-TATAGGACAGGGACGGGATG-3' SEQ ID NO:10, nt 823-842) Mr-IAG specific primers. The same set of primers was employed to address the Mr-IAG temporal expression pattern using RNA extracted as above from the base of the fifth walking legs (the approximate location of the AG in a male M. rosenbergii) of juvenile ($PL_{110-120}$) and mature males and females. M. rosenbergii β-actin was used as a positive control utilizing specific forward (5'-GAGACCT-TCAACAC CCCAGC-3' SEQ ID NO:11, nt 414-433) and reverse (5'-TAGGTGGTCTCGTGAATGC C-3' SEQ ID NO:12, nt 858-877) primers. M. rosenbergii sperm duct specifically expressed the gene Mar-SRR, accession number DQ066890, which was employed as an internal control using specific forward (5'-TCTCTGAAGCTGCAAGTGATT-TAC-3' SEQ ID NO:13, nt 144-167) and reverse (5'-AATCTGGGTCATTCTCCTGATTGG-3' SEQ ID NO:14, nt 449-472) primers. RT-PCR products were electrophoresed in 1.2% agarose gels including ethidium bromide and visualized by UV light transmission.

Northern Blot Analysis

Total RNA was isolated from the sperm duct, testis, muscle, hepatopancreas and hAG of adult males. Five micrograms of RNA from each organ were electrophoresed through a 1% agarose formaldehyde gel, transferred to a nitrocellulose membrane, and UV-cross-linked. The blot was pre-hybridized overnight and radiolabeled with a $^{32}P$ probe prepared by adding $\gamma^{32}P$-dCTP (Amersham), together with a Mr-IAG PCR product (nt 680-842; SEQ ID NO:15) to a random priming labeling mix (Biological Industries). The blot was incubated overnight in hybridization buffer containing $^{32}P$-labeled DNA. The membrane was washed and exposed to BioMax MS Kodak film with intensifying screens at −80° C. for 2.5 hr. Ribosomal RNA was visualized with ethidium bromide and UV light transmission.

Real-Time RT-PCR

RNA from the AGs of mature M. rosenbergii males from different morphotypes was extracted as disclosed herein above. RNA was then quantified by spectrophotometry at 260 nm (GeneQuant Pro, Amersham Pharmacia Biotech). First-strand cDNA was synthesized by RT reaction (Reverse-It™ $1^{st}$ strand synthesis kit-ABgene AB-0789) from 1 µg of total RNA at 47° C. for 30 min with random hexamers as primers (20 ng/µl). Using the primer express software v2.0, specific primers were designed for Mr-IAG gene (forward primer 5'-TCCCGTCCCTGTCCTATACTTG-3' SEQ ID NO:16, nt 824-846, reverse primer 5'-CGGTGATTTG ACTTTGAG-CATC-3' SEQ ID NO:17 nt 853-874) and 18S ribosomal RNA (accession number AY461599; forward primer 5'-GAAACGGCTACCACATCCAAG3' SEQ ID NO:18, nt 220-240; reverse primer 5'-GATTGGGTAATTTGCGT-GCC-3' SEQ ID NO:19, nt 251-270). Relative quantification of Mr-IAG gene was performed by using the Mr-IAG primers described above and SYBER Green PCR Master Mix (Applied Biosystems) according to manufacturer's instructions (ABI Prism 7000 Sequence Detection System, Applied Biosystems). The data obtained was normalized twice according to the sperm duct and to the 18S ribosomal RNA level. Normalized data was then expressed as $2^{-\Delta\Delta ct}$.

In Situ Hybridization

The hAGs attached to ~0.5 cm of the terminal ampullae were dissected and prepared as described by Shechter et al. (Biol. Reprod. 73, 72-79, 2005). Digoxygenin (DIG)-labeled oligonucleotides for antisense and sense probes corresponding to nucleotides 29-1745 of Mr-IAG cDNA of SEQ ID NO:1 were synthesized using SP6 and T7 RNA polymerases and the probes were hydrolyzed to reduce their length to ~200 bp as described in DIG Application Manual (Roche Applied Science) (SEQ ID NOs: 33 and 34). Hybridization was carried out as described by Shechter et al. (ibid.), with the one modification, i.e., the addition of 100 µg/ml tRNA to the hybridization solution.

Results

The reproductive tract of endocrinologically induced males did not seem morphologically different from that of intact males (FIG. 1A), however, their AG was visibly enlarged (FIG. 1B). In the intact male, a cross section of the terminal ampulae with the adjacent AG showed loose connective tissue with a small cluster of glandular cells (FIGS. 1C, 1E). In the endocrinologically induced male, the AG showed an increased number of glandular cells occupying the loose connective tissue (FIGS. 1D, 1F).

Thirty enlarged hAGs from mature BC *M. rosenbergii* males served to construct a cDNA subtractive library. Bioinformatics analysis of twenty DNA ESTs revealed a 729 bp DNA sequence with high similarity to the A chain of the putative Cq-IAG (Manor et al., ibid.). Using 5' and 3' RACE the full sequence of the cDNA of *M. rosenbergii*-insulin like AG termed Mr-IAG (SEQ ID NO:1) was found to be 1824 bp long (FIG. 2). The predicted polypeptide of this cDNA (representing a predicted pre-pro-hormone) contains 173 amino acids (SEQ ID NO:3) and has a mass of 19.76 kDa. The Mr-IAG polypeptide has structural homology to the insulin-like family of proteins, namely a signal peptide at the N'-terminus (27 amino acids), B and A chains (42 and 46 amino acids, respectively) containing 6 cysteine residues aligned with other insulin-like growth factors, the B and A chains separated by a C peptide (58 amino acids) with predicted arginine C proteinase cleavage sites at both its N' and C'-termini (FIG. 2).

The predicted B and A chains along with the C peptide (the predicted pro-hormone) is estimated to have a mass of 16.8 kDa. The predicted B and A chains that form the predicted mature protein, with a predicted mass of 9.98 kDa, were compared with those of other insulin-like factors that were also shown to be specifically transcribed in crustacean AGs (FIG. 4). The cysteine residues skeleton, typical for the insulin family of hormones, is conserved in all six sequences (FIG. 4A). The two sequences of the genus *Parcel°* of the isopoda order (*P. dilatatus*, accession number BAC57013 and *P. scaber*, accession number AAO11675) share high sequence similarity (90.8% similarity in 76 amino acids, calculated by LALIGN server). The third member of the isopoda order, *Armadillidium vulgare* (accession number BAA86893) has higher sequence similarity with the other two isopods (81.3% similarity in 75 amino acids with *P. dilatatus* and 78.7% similarity in 75 amino acids with *P. scaber*) but is less similar to the decapod sequences—Cq-IAG from *C. quadricarinatus* (25.0% similarity in 72 amino acids) and Mr-IAG from *M. rosenbergii* (28.9% similarity in 75 amino acids). The decapod species share little sequence similarity among themselves (29.1% in 86 amino acids) and with the two isopods. The sequences were subjected to the CLUSTAL W algorithm and a phylogram was calculated (FIG. 4B). The phylogram emphasizes the sequence similarity of the two isopods from the genus *Porcellio* as opposed to the great distance between them and the decapods. The third isopod species occupy another branch, closer to the decapod species sequences but nevertheless quite remote from them.

The Mr-IAG transcript was shown by RT-PCR to be exclusively expressed in the AG of sexually mature *M. rosenbergii* males and also in sexually immature males, as young as 110-120 days post larvae ($PL_{110-120}$). RT-PCR showed no signal of this gene transcription in females or in any other mature male tissues, including sperm duct, testis, thoracic ganglia, muscle and hepatopancreas (FIG. 5A). In all the tissues examined, primers for fl-actin of *M. rosenbergii* (accession number AF221096) were used as a positive control for the RT-PCR procedure. The gene Mar-SRR (accession number DQ066890) that was previously reported to be specifically transcribed in the sperm duct of *M. rosenbergii* was also used as an internal positive control for being uniquely transcribed in sperm duct and not in the AG.

Figure 5B:
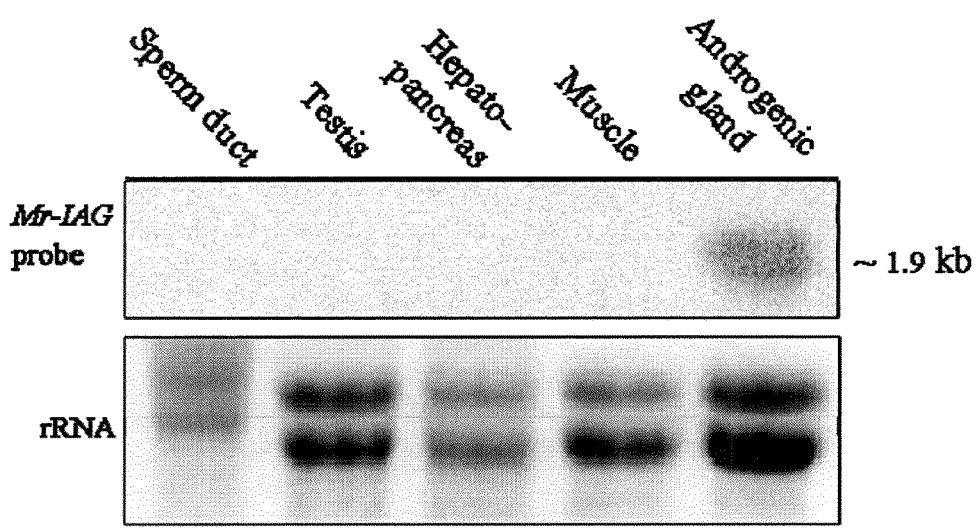

Mr-IAG gene transcript size and its AG specificity were further assessed using northern blot hybridization analysis which exhibited a single band of approximately 1.9 kb exclusively in the AG, with no signal detected in the sperm duct, testis, muscle and hepatopancreas of a mature *M. rosenbergii* male (FIG. 5B).

Figure 6A:
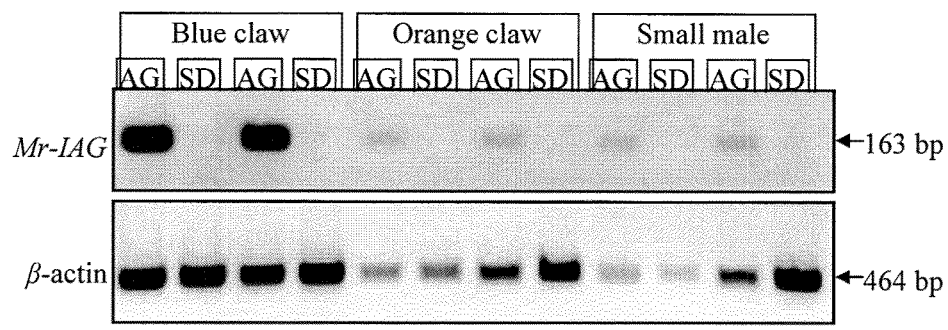
FIGS. 6A-C show the Mr-IAG transcript level in different. *M. rosenbergii* male morphotypes.
Figure 6B:
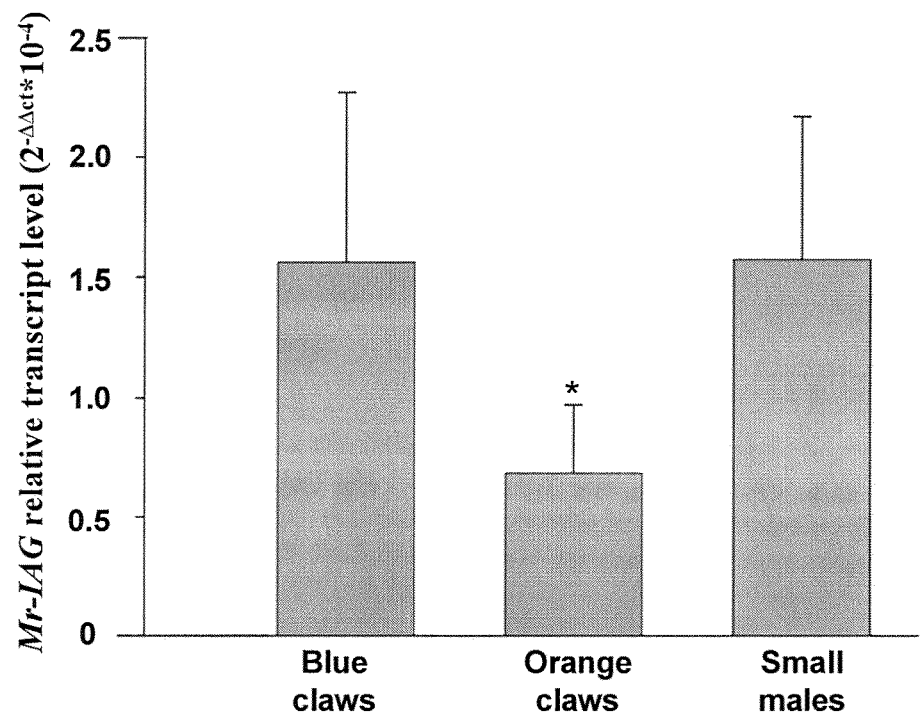

Preliminary RT-PCR results showed that the Mr-IAG gene is specifically expressed in the AG of all three *M. rosenbergii* mature male morphotypes (FIG. 6A). Real time RT-PCR showed a statistically significant (one-way ANOVA, followed by Fisher's LSD, $p<0.05$) lower Mr-IAG transcript level in AGs from OC males (n=8), compared with similar transcript levels in the AGs from the BC and SM morphotypes (n=7 each; FIG. 6B).

Figure 6C:
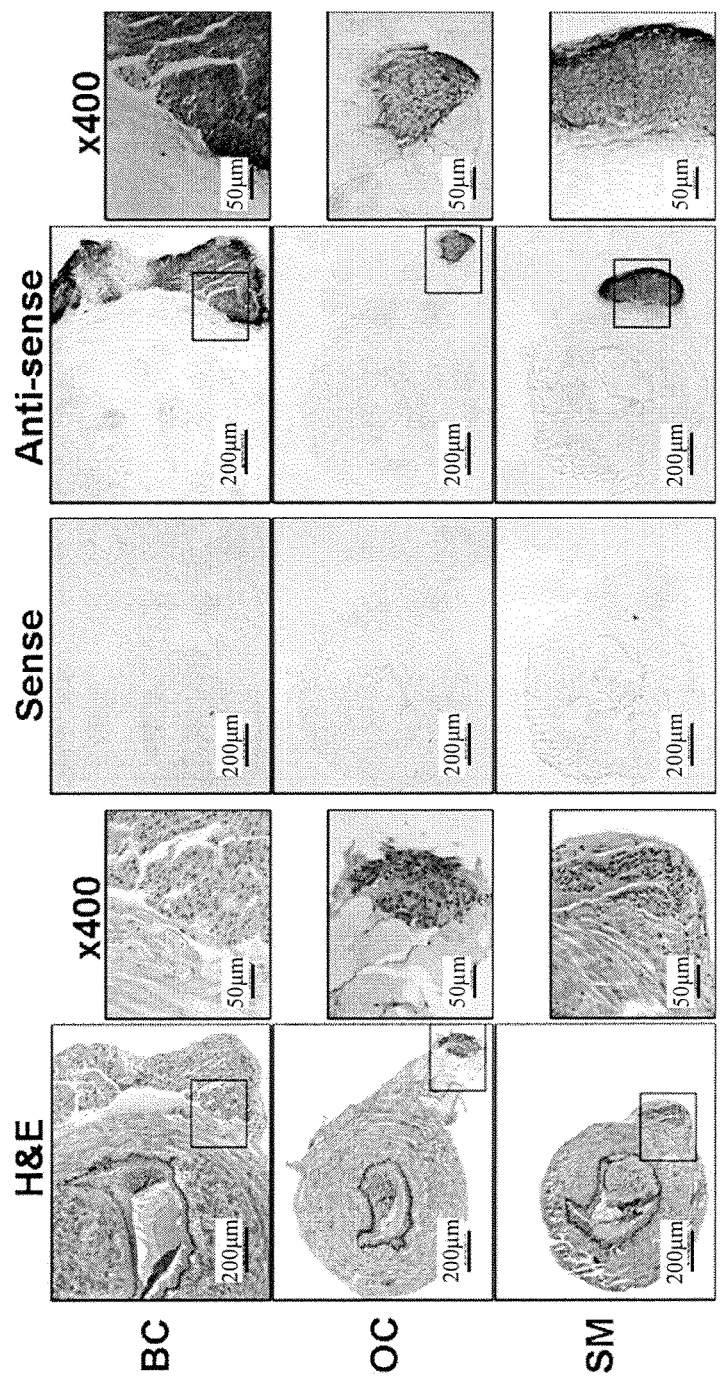

Localization of Mr-IAG in situ further confirmed its AG-specific expression (FIG. 6C). A strong, specific signal was detected exclusively in AG cells by using an antisense probe. No signal was detected when the sense-strand probe was employed.

Example 2

Silencing of Mr-IAG Gene Expression by dsRNA of SEQ ID NOs: 33 and 34 PCR Amplicon Templates for Double Stranded RNA Preparation PCR (94° C. for 3 min followed by 35 cycles of 94° C. for 30 seconds, 57° C. for 30 seconds and 72° C. for 1 minute, followed by 72° C. for 10 minutes) with plasmids containing GFP or Mr-IAG open reading frame as template, were primed by two gene specific primers with T7 promoter site at the 5' of one primer (T7P; 5'-TAATACGACTCACTATAGGG-3' SEQ ID NO:20). Primer pairs used were as follows: for Mr-IAG sense RNA synthesis: primer T7PF (5'-T7PATGGGATACTGGAA TGCCGAG-3' SEQ ID NO:21) vs. primer R (5'-CTGGAACTGCAGGTGTTAACG-3' SEQ ID NO:22). For Mr-IAG anti-sense RNA synthesis: primer F (5'-ATGGGATACTG GAATGCCGAG-3' SEQ ID NO:23) vs. primer T7PR (5'-T7PCTGGAACTGCAGGTGT TAACG-3' SEQ ID NO:24). For GFP sense RNA synthesis: primer T7 PF (5'-T7PATGG TGAGCAAGGGCGAG-3' SEQ ID NO:25) vs. primer R (5'-TGTACAGCTCGTCCATG CC-3' SEQ ID NO:26). For GFP anti-sense RNA synthesis: primer F (5'-ATGGTGAGC AAGGGCGAG-3' SEQ ID NO:27) vs. primer T7PR (5'-T7PTGTACAGCTCGTCCATG CC-3' SEQ ID NO:28). PCR amplicons were subjected to electrophoresis on a 1.2% agarose gel, viewed with ethidium bromide using UV light, excised from the gel and purified using QIAquick PCR Purification Kit (QIAGEN). The purified amplicons were used as templates for RNA synthesis. Single stranded RNA was synthesized with MEGAscript® T7 kit (Ambion) according to manufacturer's instructions, followed by DNase treatment, phenol:chloroform purification and isopropanol precipitation as recommended in the kit. RNA was quantified and diluted to 1 µg/µl and then the two strands were hybridized by heating to 70° C. for 10 minutes, followed by room temperature incubation for 10 minutes. dsRNA was kept in −20° C. until used.

In Vivo Mr-IAG Silencing (Short-Term)

For the short-term in vivo dsRNA (SEQ ID NOs: 33 and 34) injection experiment, 46 $PL_{130-140}$ *M. rosenbergii* males ranging from 0.6 to 2.1 g were size dispersed into three groups—Mr-IAG dsRNA injected (n=16), GFP dsRNA injected (n=15) and saline injected (n=15), each group was kept in a separate floating fenestrated plastic container. Before the start of the experiment, the second pleopod of each animal was removed, and the presence of the appendix masculina (AM) was confirmed under a light microscope. Twice a week (over a period of 4 weeks) each animal was injected with 5 µg dsRNA/1 g or 5 mg of GFP dsRNA or similar volumes of saline to the saline group. Molts were recorded and the regeneration of appendix masculina (AM) was viewed under a dissecting stereoscope.

For the long-term in vivo experiment, the same procedure was repeated with 36 $PL_{70-80}$ males (each weighing 0.25-1.6 g), assigned to two equal-sized groups: Mr-IAG dsRNA injected (n=18) and vehicle injected (n=18). The injection regime comprised a total of 22 injections, with the injections being given three times a week over a period of 55 days. dsRNA was injected into the sinus between the third and fourth walking legs.

In-Vivo Injection of dsRNA (SEQ ID NOs: 33 and 34) (Time-Dependent Silencing Experiment)

For time-dependent silencing experiment, young male prawns (2.49 g±0.17 SEM) were divided into four groups, of which one was injected once with exogenous RB™ dsRNA (n=5; Beeologics, Israel) as a control group, while individuals from all other three groups were injected once with Mr-IAG dsRNA (n=4; 5 µg dsRNA/g body weight for each individual). AGs from individuals of each of the three Mr-IAG dsRNA-injected groups were taken for RNA extraction 3 days, 1 week and 2 weeks after the injection, parallel to AGs taken from RB™ dsRNA-injected individuals at each time.

For dose-dependent silencing experiment, young male prawns (1.89 g±0.21 SEM) were divided into four groups, of which one was injected once with RB™ dsRNA (n=7) as a control group, while individuals from all other three groups (n=6 in each) were injected once with Mr-IAG dsRNA at different quantities as follows: 5, 1 and 0.1 µg dsRNA/g body weight. One week following injection, AGs were taken for RNA extraction from all individuals.

RNA Extraction and Real-Time RT-PCR

RNA was extracted from the AGs of males used in the time and dose dependency experiments. Total RNA was isolated with the EZ-RNA Total RNA Isolation Kit, according to the manufacturer's instructions (Biological Industries, Beit Haemek, Israel). First-strand cDNA was synthesized by means of reverse transcriptase reaction using the Verso™ cDNA Kit (Thermo Fisher Scientific Inc.) with 1 µg of total RNA. RQ of Mr-IAG transcript levels were obtained using the following primers: IAG qPCR F: 5'-GCCTTGCAGTCATCCTTGA-3' (SEQ ID NO: 29) and IAG qPCR_R: 5'-AGGCCG-GAGAGAAGAATGTT-3' (SEQ ID NO:30) with the Fast-Start Universal Probe Master (Rox) (Roche Diagnostics GmbH) and Universal ProbeLibrary Probe #144 (Roche). Mr-18S (accession no. GQ131934), which was used as a normalizing gene, was also quantified by means of real-time RT-PCR using the primers: qMr-18S_F: 5'-CCCTAAAC-GATGCTGACTAGC-3' (SEQ ID NO:31) and qMr-18S_R: 5'-TACCCCCGGAACTCAAAGA-3' (SEQ ID NO:32) with the above-mentioned mix and Universal ProbeLibrary Probe #152 (Roche). Reactions were performed with the ABI Prism 7300 Sequence Detection System (Applied Biosystems, Foster city, CA, USA).

Statistical Analyses

The four groups in the real-time RT-PCR were analyzed using the Kruskal-Wallis Test followed by the correction of a multiple pair-wise comparison (built-in within the STATISTICA software) as accepted.

Results

Figure 14A:
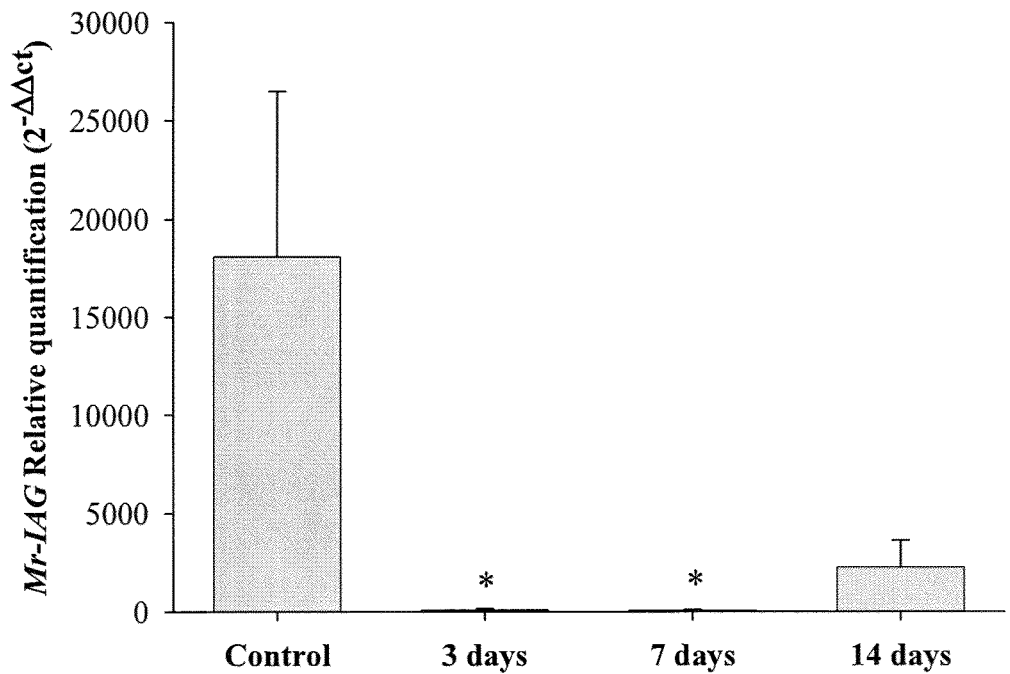
FIGS. 14A-B show relative Mr-IAG transcript levels quantified by real-time RT-PCR after a single injection of Mr-IAG dsRNA.

Real-time RT-PCR performed on RNA extracted from AGs of individuals injected with Mr-IAG dsRNA (5 µg/g body weight) at different time periods after the injection showed that Mr-IAG silencing effect at the transcript level is effectively sustained up to one week (FIG. 14A).

Figure 14B:
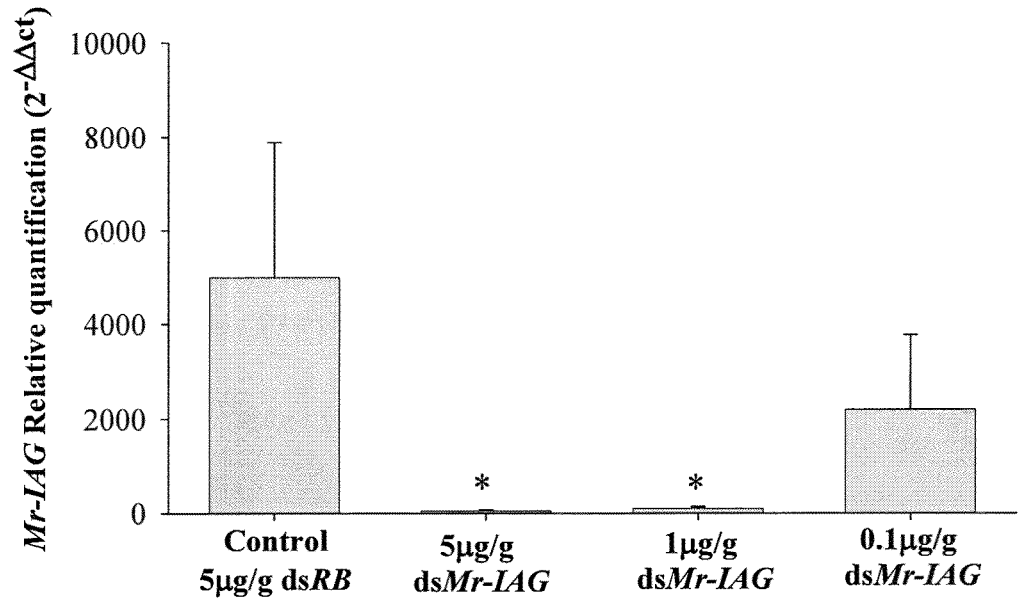

Real-time RT-PCR performed a week after injection of different Mr-IAG dsRNA doses showed that 1 µg of Mr-IAG dsRNA/g body weight is sufficient for effectively silencing the Mr-IAG (FIG. 14B). Thus, injection of Mr-IAG dsRNA to young male prawns reduced or down regulated the expression of Mr-IAG.

Statistical Analysis

To evaluate the effect of dsRNA injection on the rate of AM regeneration and on the molt interval, a Cox proportional hazards regression model was used. The model is expressed by: $\mu(t; z)=\mu_0(t)\exp(\Sigma\beta_i z_i)$, where $\mu(t,z)$ is AM regeneration rate and $\mu_0(t)$ is the baseline hazard function which can change over time (t). The regression coefficient to be estimated, $\beta_i$, represents the independent effect of dsRNA injection on AM regeneration rate. These analyses were performed with S-PLUS 2000. The effect of dsRNA injection on molt increment was statistically analyzed by paired t-test using Statistica 6.1 software.

Results

Figure 7:
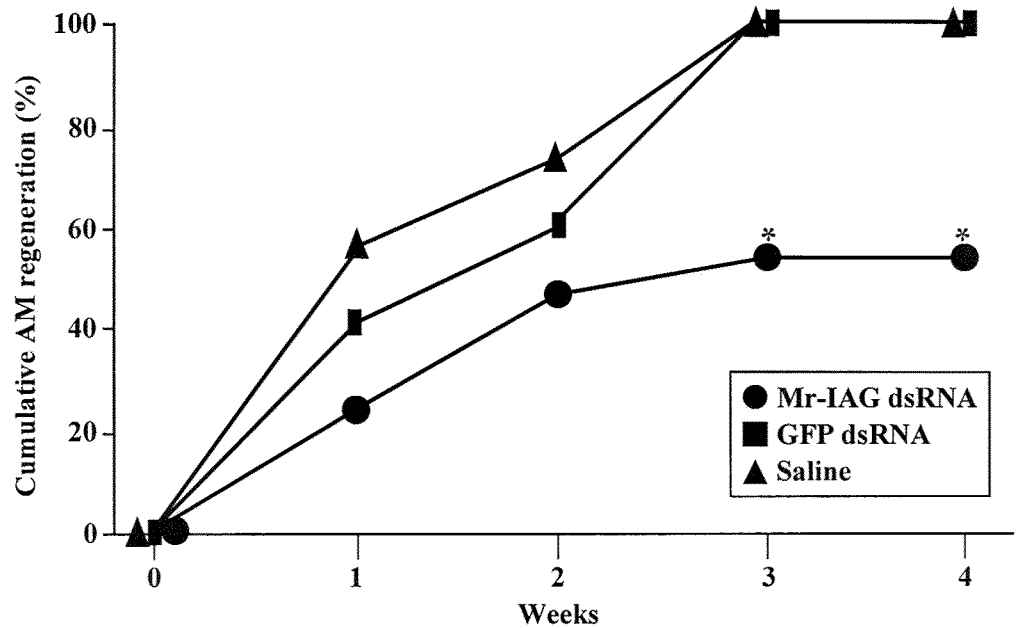
FIG. 7 shows the cumulative appendix masculina (AM) regeneration of in vivo dsRNA injected *M. rosenbergii* males. Cumulative AM regeneration proportion over time in weeks represented as percentage for experimental Mr-IAG dsRNA (●), GFP dsRNA (■) and saline (▲) injected groups. Asterisk points significant difference between Mr-IAG dsRNA injected group and the two control groups.

In the short RNAi experiment (silencing via in vivo dsRNA injection of SEQ ID NOs: 33 and 34), growth parameters (weight accumulation, molts) in the dsRNA injected *M. rosenbergii* males were insignificantly different between groups. By the third week, all individuals in the two control groups regenerated their appendix masculinae (AM; 13 in the saline injected group and 12 in the GFP dsRNA injected group). In the Mr-IAG dsRNA injected group, 6/13 did not regenerate their AM neither by the third week nor by the forth week (FIG. 7). Statistical analysis (Cox proportional hazards regression model) revealed significant difference between dsRNA Mr-IAG injected group and the two control groups (z=1.98, p=0.048 compared with GFP injected group and z=2.33, p=0.02 compared with saline injected group). No significant difference was observed between the two control groups.

Figure 8A:
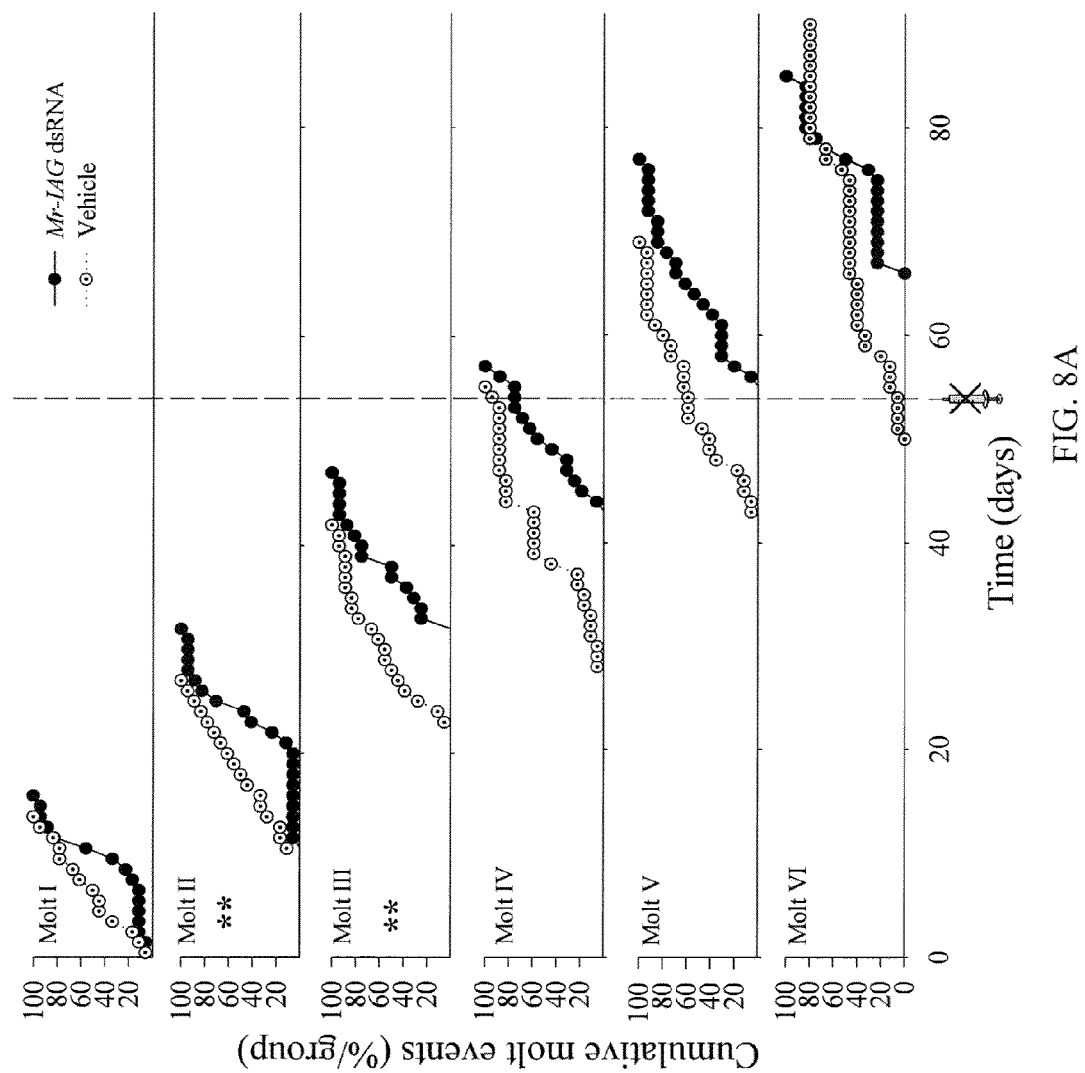
FIGS. 8A-B show the effects of Mr-IAG dsRNA injection on molt and growth of young *M. rosenbergii* males.
Figure 8B:
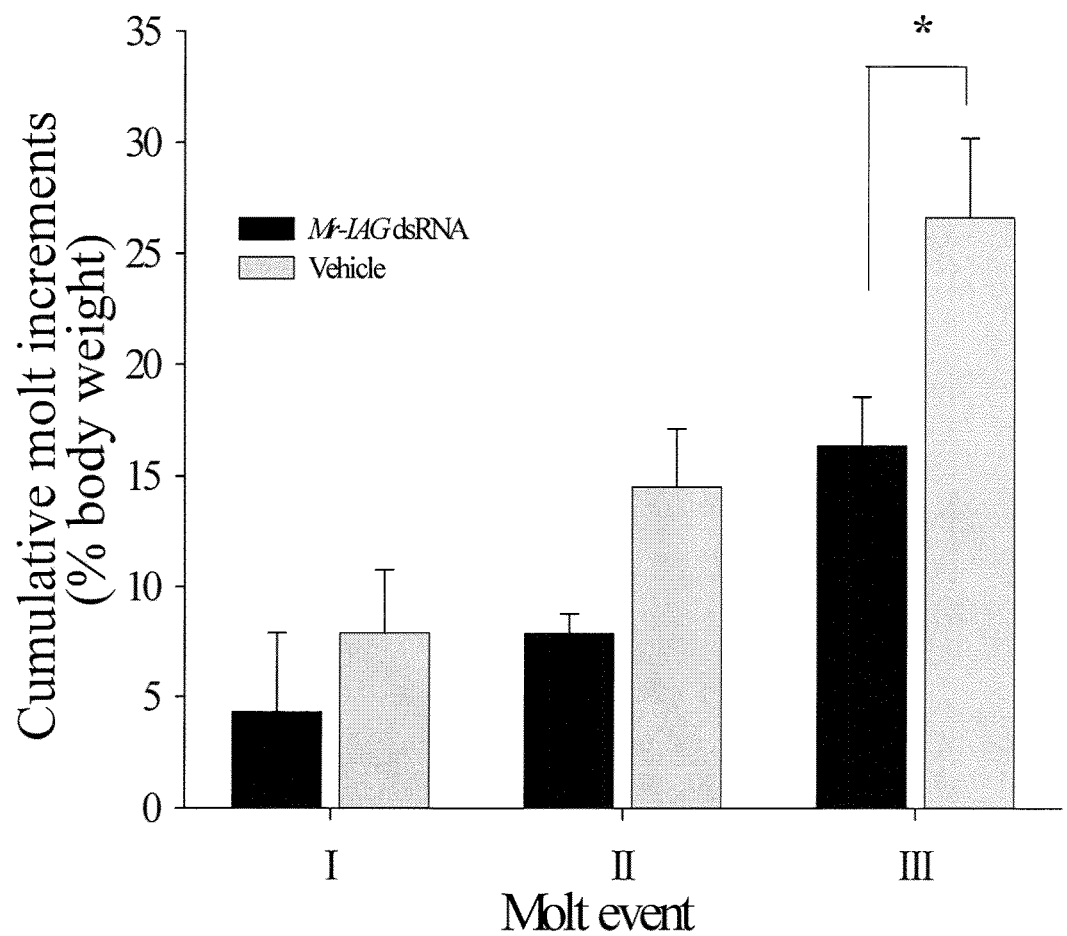

As the GFP-dsRNA-injected and vehicle-injected control groups did not differ significantly from one another, the long-term in vivo dsRNA injection assay included only a vehicle-injected control group and the Mr-IAG-dsRNA-injected group. In the long-term experiment, all individuals had molted at least three times by the end of the injection period (day 55), thus statistical analysis was applied only for the first three molt events. FIG. 8A shows that cumulative molt events were significantly different between groups (Cox proportional hazards regression model; second molt z=2.59, p=0.0097; third molt z=3.07, p=0.0021). From the time of the first molt event, the Mr-IAG-dsRNA-injected group lagged in molt intervals behind the vehicle-injected group, with the most marked lag being that between the first and second molts (lowest exponent coefficient; FIG. 8A). The lag was sustained even after the end of the injection period. Weight accumulation was lower in the Mr-IAG-dsRNA-injected group, and this difference became statistically significant by the third molt event (paired t-test, p=0.0224, FIG. 8B).

Figure 9:
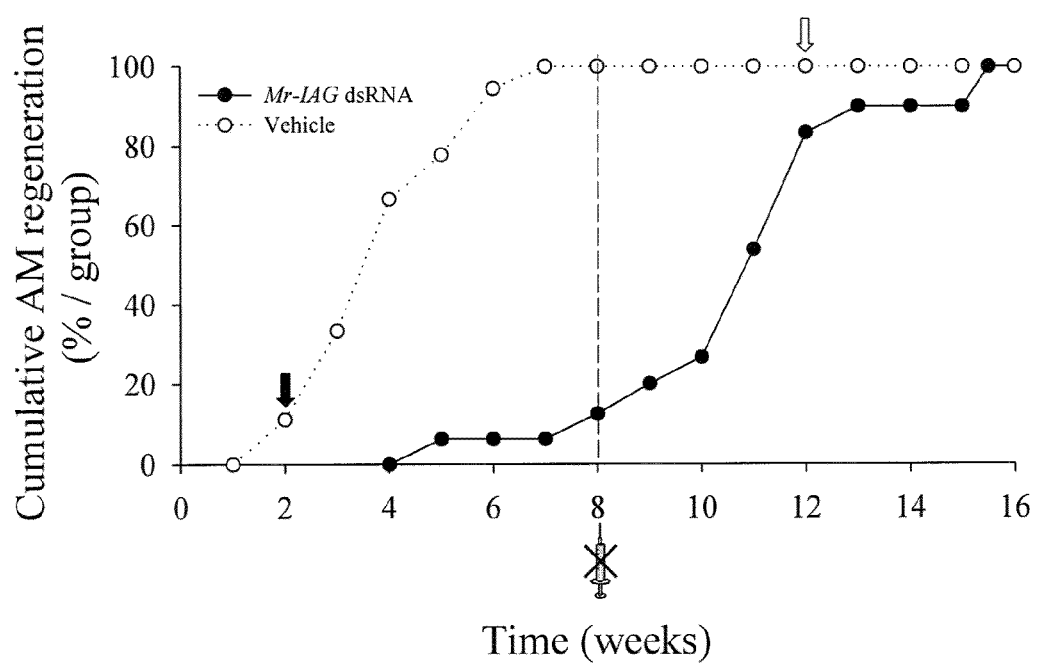
FIG. 9 shows the regeneration of the appendix masculina as a percentage of the population over 16 weeks in Mr-IAG-dsRNA-injected (●) and vehicle-injected (○) groups. The end of the repeated injection period is marked as—✻— (day 55). Bold black arrow represents the point at which statistical differences between the two groups first appeared, and the white arrow, the point from which there was no statistical difference (i.e., recovery of the appendices masculinae in the Mr-IAG dsRNA-injected group).

In the long-term silencing experiment, the appendices masculinae of the left leg regenerated exclusively in the vehicle-injected animals: by the 44th day the appendices masculinae of all 18 control prawns had regenerated, while in the group of Mr-IA-dsRNA-injected animals, the organs of only two individuals (out of 16) had regenerated by the end of the repeated injection period (by days 32 and 53 in those two animals). The lag in the regeneration of the appendices masculinae of the animals injected with Mr-IAG dsRNA was statistically significant and consistent over the entire injection period (Cox proportional hazards regression model; z=4.03, P<0.001). By 55 days after termination of the injections, the appendices masculinae of all the animals injected with Mr-IAG dsRNA had regenerated (FIG. 9). Four weeks after the termination of the injection period, the differences between the groups were no longer statistically significant.

Serial dorsoventral sections of two representative individuals from the group of animals injected with Mr-IAG dsRNA and two from the vehicle-injected group were stained with hematoxylin & eosin (FIG. 10). Both individuals from the Mr-IAG-dsRNA-injected group showed a clear arrest of spermatogenesis, as indicated by the absence of spermatozoa in all sections of the sperm ducts and testes (FIGS. 10A and 10E). Overall, the testes of the animals receiving the Mr-IAG dsRNA injections were smaller than those of the vehicle-injected group (FIGS. 10E and 10F, respectively). The two individuals from the vehicle-injected group showed active spermatogenesis, as seen by the presence of many spermatozoa in the testis lobules and in the sperm ducts (FIGS. 10F and 10B). The spermatogenic arrest observed in the animals injected with Mr-IAG dsRNA was accompanied by hyperplasia and hypertrophy AG cells (FIG. 10C). The AG cells of the two prawns from the vehicle-injected group were fewer in number and smaller in size than those of the animals injected with the Mr-IAG dsRNA (FIGS. 10D and 10C). The number and size of the AG cells in the two vehicle-injected animals resembled those of intact males of the same age.

Example 3

Generating a Monosex Crustacean Culture

Animals

*M. rosenbergii* were maintained at Ben-Gurion University of the Negev under the following conditions: Food comprising shrimp pellets (Rangen, Buhl, ID; 30% protein) was supplied ad libitum three times a week. Water quality was assured by circulating the entire volume through a bio-filter maintaining all the required water physicochemical parameters. Egg-bearing females were separately transferred to closed 100 L tanks containing 12-16 ppt salt water, which was circulated through a 100-μm mesh net. After hatching had occurred, the females were removed from the tanks, and the newly hatched larvae were maintained according to the protocol devised by Una et al. (Tokyo University of Fisheries 55: 179-190, 1969) and fed with *Artemia nauplii* daily.

Tissue Preparation

AGs from mature male morphotypes were dissected, together with the attached terminal ampullae. Tissue samples were fixed in modified Carnoy's II for 48 h and dehydrated gradually through a series of increasing alcohol concentrations. Tissues were cleared and embedded in Paraplast (Kendall, Mansfield, Mass.) according to conventional procedures. Sections (5 μm-thick) were cut and mounted onto silane-coated slides (Menzel-Gläser, Braunschweig, Germany). These slides served for all histological procedures, including immunohistochemistry and in situ hybridization. Prior to the histological procedures, the slides were de-paraffinized in xylene and gradually rehydrated through a series of decreasing alcohol concentrations.

Genomic DNA Extraction and Sex Markers

Genomic DNA was extracted from 2-10 mg 70% ethanol-fixed tissue using a REDExtract-N-Amp Tissue PCR Kit (Sigma) according to the manufacturer's instructions. The genomic sex markers developed in the Israeli line (BGU line) were used as described (Ventura et al., Heredity, in press, 2011).

PCR of Female-Specific and Positive Control Sequences

PCR was performed with 100 ng genomic DNA, 1 μM forward primer and 1 μM reverse primer, 12.5 μL Ready Mix REDTaq (Sigma) and water to a final volume of 25 μL. The PCR conditions used were: 35 cycles of 30 s at 94° C., 30 s at 56° C. and 60 s at 72° C. PCR products were separated on a 2% agarose gel and visualized under UV light with ethidium bromide.

Preparation of dsRNA Directed to IAG (Inhibiting IAG Expression)

dsRNA of the Mr-IAG open reading frame was prepared with a MEGAscript T7 kit (Ambion, Foster city, CA) according to the manufacturer's instructions. dsRNA quality was assessed on an agarose gel. The dsRNA was maintained at −20° C. until used as previously described (Ventura et al. Endocrinology 150: 1278-1286, 2009).

In Vivo Mr-IAG Silencing $PL_{30}$ *M. rosenbergii* males and females (each weighing 30-70 mg) were selected according to the presence of the female-specific sex marker in females and its absence in males (Ventura et al., Heredity, 2011; Ventura et al., Endocrinology, Article ID 476283, 2011). The post-larvae organisms were assigned to one of three treatment groups: Mr-IAG dsRNA (SEQ ID NOs: 33 and 34)-injected males (n=19), water-injected control males (n=15), and water-injected control females (n=16). Each animal was housed in a separate floating fenestrated plastic container (3×11 cm). Twice a week (over a period of 9 months), each animal was injected with 5 μg of dsRNA/g or a similar volume of water (a total of 71 injections). Molts were recorded twice a week, and weight accumulation was documented. The appearance of male gonopores and appendix masculinae were viewed under a dissecting stereoscope.

Statistical Analysis

To evaluate the effect of dsRNA (SEQ ID NOs: 33 and 34) injections on the rate of MGP and AM appearance, a Cox proportional hazards regression model was used. The model is expressed by: $\mu(t; z) = \mu_0(t) \exp(\Sigma \beta_i z_i)$, where $\mu(t,z)$ is the MGP or AM appearance rate and $\mu_0(t)$ is the baseline hazard function that can change over time (t). The regression coefficient to be estimated, $\beta_i$, represents the independent effect of dsRNA injection on the MGP or AM appearance rate. These analyses were performed with S-PLUS 2000 software (Mathsoft, Needham, Mass.). The effect of dsRNA injection on molt increment and the weight range associated with MGP appearance were statistically analyzed by the non-parametric Mann-Whitney U test using Statistica 6.1 software (StatSoft, Tulsa, USA).

Results

Mr-IAG-Silencing Inhibits the Appearance of External Male Sexual Characters

Mr-IAG was silenced in juvenile males initially identified through the use of a genomic sex marker as early as $PL_{30}$, prior to the appearance of external sexual characteristics. Mr-IAG-silencing caused a delay in appendix masculinae (AM) formation in the Mr-IAG silenced group. This delay became significant by $PL_{128}$. By $PL_{220}$, all individuals from the control male group developed an AM, as compared with as few as 33% of the Mr-IAG-silenced male group. None of the control females developed an AM.

The appearance of male genital opening, male gonopores (MGP), was also delayed in the Mr-IAG-silenced group. By day 128, this delay became significant when compared with the control male group. By day 184, both groups included the maximum percentage of individuals with MGP and although all individuals developed MGP in the control male group, only 60% did so in the Mr-IAG-silenced group of males. None of the control females developed MGP. In four Mr-IAG-silenced individuals, MGP did not develop by day 220.

Mr-IAG-Silencing Induces Functional Sex Reversal

One of the four Mr-IAG-silenced individuals that did not develop MGP, weighing 808 mg, was sampled for histological survey, while the other three were injected until they reached a weight of 1 g, along with three control males and four control females. The rest of the Mr-IAG-silenced and control individuals were also sampled for such histological analysis. Mr-IAG-silenced individuals that have developed MGP were found to have also acquired hypertrophied AGs. When the Mr-IAG-silenced individual with no MGP (FIG. 11, middle) was compared with individual male (FIG. 11, left) and female controls (FIG. 11, right) of the same weight, clear evidence for sex reversal was observed. The Mr-IAG-silenced male resembled the control female, with both having ovaries (Mr-IAG-silenced male and control female shown in FIGS. 11D and 11G and at higher magnification in FIGS. 11E and 11H, respectively) and oviducts (Mr-IAG-silenced male and control female shown in FIGS. 11F and 11I, respectively), with no signs of testes, sperm ducts (as evident in the control male; testes in FIGS. 11A and 11B at higher magnification, sperm duct in FIG. 11C) or AGs. The three other Mr-IAG-silenced genetic males with no MGP were, on the other hand, raised to maturity and developed normal appearing ovaries (FIG. 12A, upper panel, marked by an arrow), as compared with control females.

Two of the three Mr-IAG-silenced genetic males with no MGP were mated with normal males. Their reproductive behavior was normal and copulation was successful. Specifically, the spermatophore attached by the male onto the ventral cephalothorax of the Mr-IAG-silenced genetic males was maintained. These then spawned and incubated the eggs in their brood-chambers, located ventrally on their abdomens (FIG. 12A, bottom panel, marked by an arrow. A batch of brooded eggs is magnified). These egg-bearing 'neo-females' (weighing 7.2 g and 11.54 g) were transferred to a hatching facility and in parallel, control females of approximately the same size (7.3 g and 13.11 g), were hatched. The time of egg development until hatching was similar for the 'neo-females' and the control female progeny (18 and 20 days and 15 and 20 days, respectively) as was the time from hatching to metamorphosis (22-23 days). Larval staging was similar throughout the hatching period. Thirty larvae of zoea stage 3 were sampled from each progeny for genetic sex determination using the molecular sex marker. The genetic sex of the 'neo-females' and the control females which produced the progeny was reconfirmed, as were the genetic sex of intact male and female positive controls and a negative control (FIG. 12B; marked as ♂, ♀, and n.c., respectively). All controls and reconfirmations were as expected, revealing the female-specific sex marker only in the intact and control females. The progeny of the control females were found to comprise both males and females, as expected (FIG. 12B, F1 in upper panel), while progeny of the 'neo-females' comprised only males (FIG. 12B, F1 in bottom panel).

The present results demonstrate for the first report that a single gene manipulation induces full functional sex reversal in crustaceans. The early time point at which Mr-IAG silencing was initiated in the present study, i.e., prior to the appearance of external sexual characteristics and close to the time period at which Mr-IAG starts to express, contributed to the successful sex reversal. This study provides a crustacean monosex population culture based upon AG-specific factor manipulation, i.e., the IAG, which was identified in representative species of all four major crustacean cultured groups (Chung et al., General and Comparative Endocrinology, in press, 2011; Mareddy et al., Aquaculture, in press, 2011; Manor et al., General and Comparative Endocrinology 150, 326-336, 2007), as well as on genomic sex markers that are also available for several species (Staelens et al., Genetics 179: 917-925, 2008).

Figure 13:
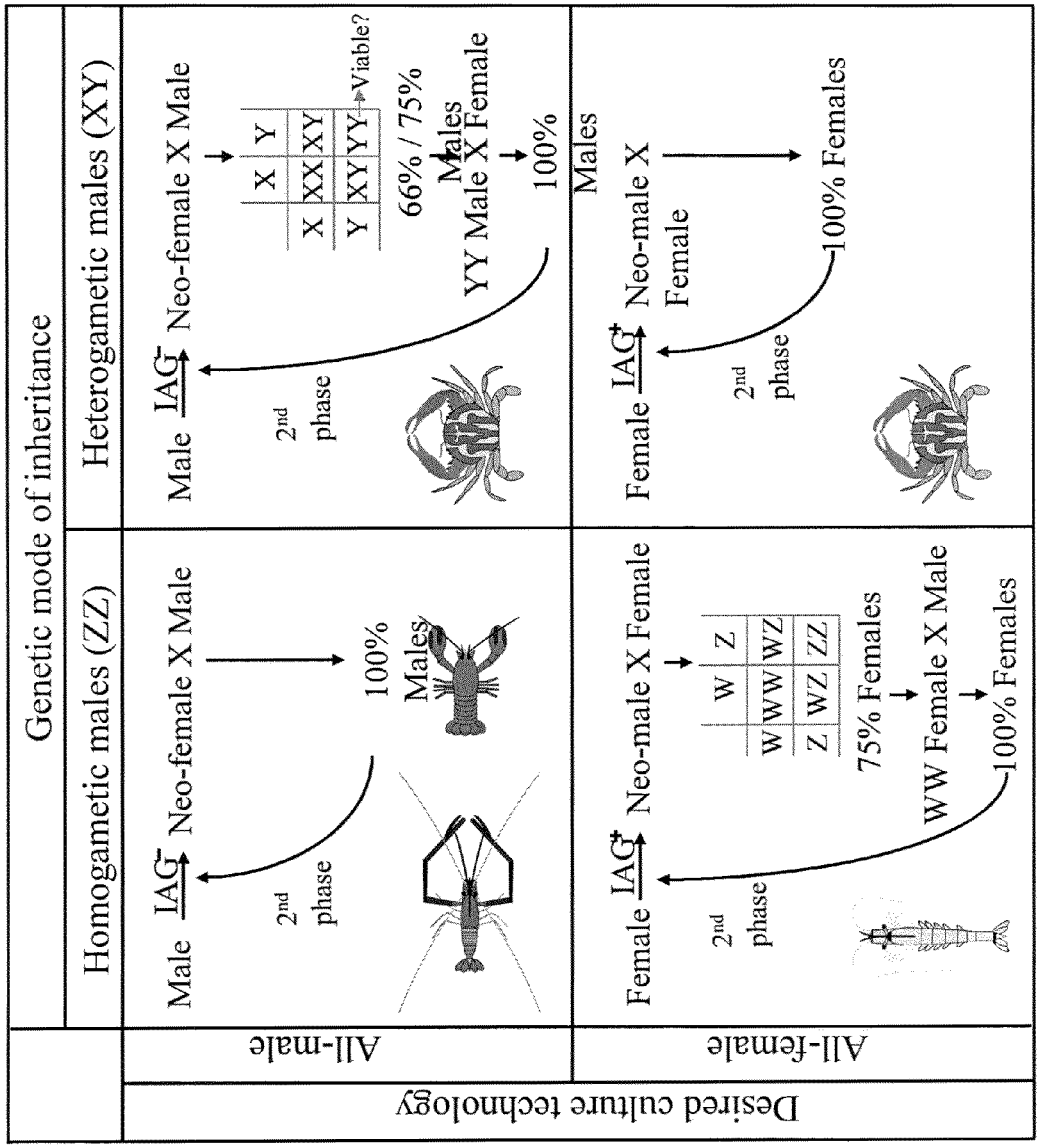
FIG. 13 shows production schemes for cultured crustacean monosex populations through IAG manipulations according to sex chromosome composition and industry preference. The IAG can be manipulated in species where males are homogametic (ZZ, left) or heterogametic (XY, right). For each scheme, representative groups of species are denoted. The IAG can be either removed from males to obtain neo-females (top) or administered to females to obtain neo-males (bottom).

Thus, IAG manipulation can yield improved production of crustaceans through monosex culture. TAG expression can be either knocked down in males to obtain neo-females as described herein above, or administered to females, to obtain neo-males. In species where males are homo/heterogametic, IAG removal/administration can be performed. Where males are homogametic (i.e., bear two homologous sex chromosomes, ZZ), and where males are the preferred sex for culture, as in crayfish and prawn, IAG deprivation from males to induce neo-females will enable 100% male population production as was achieved in the present example (FIG. 13, top left). Where males are homogametic and females are the preferred cultured sex, as in shrimp, IAG administration to females, designed to induce neo-males, will enable a 100% female population (FIG. 13, bottom left), as supported by findings in crayfish showing that WW females are viable and are able to reproduce. The same set of IAG interventions are also feasible in heterogametic males, like crabs (FIG. 13, right). However, since YY males were not shown to be viable, an all-female population production scheme is simpler to achieve than is an all-male strategy. Moreover, as all-female production is economically beneficial, all-female population culture should be the preferred approach taken in the case of crabs (FIG. 13, bottom right).

It will be appreciated by persons skilled in the art that the present invention is not limited by what has been particularly shown and described herein above. Rather the scope of the invention is defined by the claims that follow.

The invention claimed is:

1. A method for obtaining a neofemale decapod crustacean, comprising:

Down regulating the expression of insulin-like factor gene of the androgenic gland (IAG) in an up to 180 days post-larvae old male decapod crustacean, thereby obtaining a neofemale decapod crustacean, wherein said down regulating the expression of the insulin-like factor of the androgenic gland (IAG) in said male is administering to said male an anti-sense RNA directed to IAG or a double stranded RNA molecule directed to IAG.

2. The method of claim 1, wherein said decapod crustacean is *Macrobrachium rosenbergii* (MR).

3. The method of claim 1, wherein said male decapod crustacean is from 1 to 150 days post-larvae old.

4. The method of claim 1, wherein said male decapod crustacean is from 10 to 50 days post-larvae old.

5. The method of claim 1, wherein said anti-sense RNA molecule directed to IAG or said double stranded RNA molecule directed to IAG comprises a RNA sequence corresponding to SEQ ID NO: 33 or a fragment thereof, said fragment comprises at least 21 bases.

6. A neofemale decapod crustacean obtained by the method of claim 1.

7. The neofemale of claim 6, wherein said decapod crustacean is *Macrobrachium rosenbergii* (MR).

8. A method for obtaining a decapod crustacean population comprising more than 50% males, comprising the step of breeding a male decapod crustacean with a neofemale decapod crustacean of claim 6, thereby obtaining a decapod crustacean population comprising more than 50% males.

9. The method of claim 8, wherein said decapod crustacean is *Macrobrachium rosenbergii* (MR).

10. The method of claim 8, wherein said more than 50% males is an all male population.

* * * * *

SEQUENCE LISTING

<160> NUMBER OF SEQ ID NOS: 34

<210> SEQ ID NO 1
<211> LENGTH: 1824
<212> TYPE: DNA
<213> ORGANISM: Macrobrachium rosenbergii

<400> SEQUENCE: 1

```
ggttattcca agagggggcca agactctggg atcacacctc gaacggctct gtcccttccc    60
ctcgtccgtt taaccggtgt tttctagcca cgctctcaac acctaaaaat tccctctctt   120
gctttctggc cagccttgca gtcatccttg aaattccctc ttccttatat ttcgggacat   180
aacattcttc tctccggcct tttcatatcg aagtgaaaca atcaactac agaatgggat    240
actggaatgc cgagatcaag tgtgtgttgt tctgctcact cgtagcatcg cttctccctc   300
aaccttcttc gagctatgag atcgaatgcc tctccgttga cttttgactgc ggcgacataa   360
cgaacaccct tgcctccgtc tgcctgagac acaacaacta catcaaccca ggacccacct   420
acgtttccaa agagcgacga tctgctgaca tctataccgt tccttctacg aagtctccat   480
cgctcgccca cccgagagct acccacttga ccatggctga cgaagaaact cagaaggtat   540
ctaaggtgga ggaggagatt cagcacatga cgctgagcag ggaagaagcg aacaatatgc   600
tgcattcgaa gcgtcgcttc cggagggaca gcgtgaggag aagtccaagg gaggaatgct   660
gcaacaacgc ctcttttcaga cgctgcaact tcgaggaagt cgccgaatat tgcatcgagc   720
tgcgtcccgg cgttaacacc tgcagttcca ggtaggaggc tcaaggatc atcccgtccc    780
tgtcctatac ttgacaggag atgctcaaag tcaaatcacc gtcttcgagt catgatgtgg   840
aatgaccttc agctaaagct gccttttggc tttcctcaca gtcaactaaa acaattttt   900
tttatcctac cgttaccttc agataaatta ttcctttgtc tcagctttaa tttcggctaa   960
agcttttttt tttgttctac ccatgcattc agctaaagct ttcttttgtt tcgccttta  1020
attcaacact cctctgcctt acccttattt cagctaatgg cttctttta ttttaccatt  1080
accatccaca aagctttgtt tgtcttacc ctcagctgaa acgtttgttt gtctcacctt  1140
taccctcagc taaaactttc ttttgtcttc ccgctgcttt agtaaatgct ttcttctgtc  1200
acactttttac tttcagctag ggattctttt tttttttttg ccacttttac cttcagctaa  1260
agggtactat tgtctcaccc ttgccttctg ctaaaggttc cttttgtccc acccttgcct  1320
tcaactaaag gttccttttg tctcacccct gccttcagct aaaggttcct tttgtctcac  1380
ccttgccttc agctaaaggt tccttttgtc tcacccttgc cttcagccaa aggttccttt  1440
tgtctcaccc ttgccttcag ctaaaggttc catttgtctc acctttgcct tcagctaaag  1500
gttccttttg tctcacccctt gccttcagct aaaggtccct tttgtctcac ccgtgcatcc  1560
aactaaaggt tccttttacc tctcttttat ctttaactaa agttttttgt ttttgtatcc  1620
ttgccttcag ccaaacgttc ttttgtttta tctttacacg caacaacatc tagacatttc  1680
caaacattaa gcatattgca ttattattgg tgattcttgt cgatgtttcc gaaaaattgt  1740
ttgatacatc agttatacgt caaataaatg cttttgagaa cccggaaaaa aaaaagaaa  1800
aaaaaaaaa aaaaaaaaaa aaaa                                           1824
```

<210> SEQ ID NO 2
<211> LENGTH: 519
<212> TYPE: DNA
<213> ORGANISM: Macrobrachium rosenbergii

<400> SEQUENCE: 2

```
atgggatact ggaatgccga gatcaagtgt gtgttgttct gctcactcgt agcatcgctt     60
ctccctcaac cttcttcgag ctatgagatc gaatgcctct ccgttgactt tgactgcggc   120
gacataacga cacccttgc ctccgtctgc ctgagacaca caactacat caacccagga    180
cccacctacg tttccaaaga gcgacgatct gctgacatct ataccgttcc ttctacgaag   240
```

-continued

| | |
|---|---|
| tctccatcgc tcgcccaccc gagagctacc cacttgacca tggctgacga agaaactcag | 300 |
| aaggtatcta aggtggagga ggagattcag cacatgacgc tgagcaggga agaagcgaac | 360 |
| aatatgctgc attcgaagcg tcgcttccgg agggacagcg tgaggagaag tccaagggag | 420 |
| gaatgctgca acaacgcctc tttcagacgc tgcaacttcg aggaagtcgc cgaatattgc | 480 |
| atcgagctgc gtcccggcgt taacacctgc agttccagg | 519 |

<210> SEQ ID NO 3
<211> LENGTH: 438
<212> TYPE: DNA
<213> ORGANISM: Macrobrachium rosenbergii

<400> SEQUENCE: 3

| | |
|---|---|
| tatgagatcg aatgcctctc cgttgacttt gactgcggcg acataacgaa caccccttgcc | 60 |
| tccgtctgcc tgagacacaa caactacatc aacccaggac ccacctacgt ttccaaagag | 120 |
| cgacgatctg ctgacatcta taccgttcct tctacgaagt ctccatcgct cgcccacccg | 180 |
| agagctaccc acttgaccat ggctgacgaa gaaactcaga aggtatctaa ggtggaggag | 240 |
| gagattcagc acatgacgct gagcagggaa gaagcgaaca atatgctgca ttcgaagcgt | 300 |
| cgcttccgga gggacagcgt gaggagaagt ccaagggagg aatgctgcaa caacgcctct | 360 |
| ttcagacgct gcaacttcga ggaagtcgcc gaatattgca tcgagctgcg tcccggcgtt | 420 |
| aacacctgca gttccagg | 438 |

<210> SEQ ID NO 4
<211> LENGTH: 264
<212> TYPE: DNA
<213> ORGANISM: Macrobrachium rosenbergii

<400> SEQUENCE: 4

| | |
|---|---|
| tatgagatcg aatgcctctc cgttgacttt gactgcggcg acataacgaa caccccttgcc | 60 |
| tccgtctgcc tgagacacaa caactacatc aacccaggac ccacctacgt ttccaaagag | 120 |
| cgacgacgct tccggaggga cagcgtgagg agaagtccaa gggaggaatg ctgcaacaac | 180 |
| gcctctttca gacgctgcaa cttcgaggaa gtcgccgaat attgcatcga gctgcgtccc | 240 |
| ggcgttaaca cctgcagttc cagg | 264 |

<210> SEQ ID NO 5
<211> LENGTH: 173
<212> TYPE: PRT
<213> ORGANISM: Macrobrachium rosenbergii

<400> SEQUENCE: 5

Met Gly Tyr Trp Asn Ala Glu Ile Lys Cys Val Leu Phe Cys Ser Leu
1               5                   10                  15

Val Ala Ser Leu Leu Pro Gln Pro Ser Ser Tyr Glu Ile Glu Cys
            20                  25                  30

Leu Ser Val Asp Phe Asp Cys Gly Asp Ile Thr Asn Thr Leu Ala Ser
        35                  40                  45

Val Cys Leu Arg His Asn Asn Tyr Ile Asn Pro Gly Pro Thr Tyr Val
    50                  55                  60

Ser Lys Glu Arg Arg Ser Ala Asp Ile Tyr Thr Val Pro Ser Thr Lys
65                  70                  75                  80

Ser Pro Ser Leu Ala His Pro Arg Ala Thr His Leu Thr Met Ala Asp
                85                  90                  95

Glu Glu Thr Gln Lys Val Ser Lys Val Glu Glu Glu Ile Gln His Met

```
                       100                 105                 110
Thr Leu Ser Arg Glu Glu Ala Asn Asn Met Leu His Ser Lys Arg Arg
            115                 120                 125

Phe Arg Arg Asp Ser Val Arg Arg Ser Pro Arg Glu Glu Cys Cys Asn
        130                 135                 140

Asn Ala Ser Phe Arg Arg Cys Asn Phe Glu Glu Val Ala Glu Tyr Cys
145                 150                 155                 160

Ile Glu Leu Arg Pro Gly Val Asn Thr Cys Ser Ser Arg
                165                 170

<210> SEQ ID NO 6
<211> LENGTH: 88
<212> TYPE: PRT
<213> ORGANISM: Macrobrachium rosenbergii

<400> SEQUENCE: 6

Tyr Glu Ile Glu Cys Leu Ser Val Asp Phe Asp Cys Gly Asp Ile Thr
1               5                   10                  15

Asn Thr Leu Ala Ser Val Cys Leu Arg His Asn Asn Tyr Ile Asn Pro
            20                  25                  30

Gly Pro Thr Tyr Val Ser Lys Glu Arg Arg Phe Arg Arg Asp Ser
        35                  40                  45

Val Arg Arg Ser Pro Arg Glu Glu Cys Cys Asn Asn Ala Ser Phe Arg
    50                  55                  60

Arg Cys Asn Phe Glu Glu Val Ala Glu Tyr Cys Ile Glu Leu Arg Pro
65                  70                  75                  80

Gly Val Asn Thr Cys Ser Ser Arg
                85

<210> SEQ ID NO 7
<211> LENGTH: 28
<212> TYPE: DNA
<213> ORGANISM: Artificial Sequence
<220> FEATURE:
<223> OTHER INFORMATION: SYNTHETIC

<400> SEQUENCE: 7
gagcagggaa gaagcgaaca atatgctg                                          28

<210> SEQ ID NO 8
<211> LENGTH: 28
<212> TYPE: DNA
<213> ORGANISM: Artificial Sequence
<220> FEATURE:
<223> OTHER INFORMATION: SYNTHETIC

<400> SEQUENCE: 8
atcatcccgt ccctgtccta tacttgac                                          28

<210> SEQ ID NO 9
<211> LENGTH: 20
<212> TYPE: DNA
<213> ORGANISM: Artificial Sequence
<220> FEATURE:
<223> OTHER INFORMATION: SYNTHETIC

<400> SEQUENCE: 9
gacagcgtga ggagaagtcc                                                   20

<210> SEQ ID NO 10
<211> LENGTH: 20
<212> TYPE: DNA
```

<213> ORGANISM: Artificial Sequence
<220> FEATURE:
<223> OTHER INFORMATION: SYNTHETIC

<400> SEQUENCE: 10
tataggacag ggacgggatg                                            20

<210> SEQ ID NO 11
<211> LENGTH: 20
<212> TYPE: DNA
<213> ORGANISM: Artificial Sequence
<220> FEATURE:
<223> OTHER INFORMATION: SYNTHETIC

<400> SEQUENCE: 11
gagaccttca acaccccagc                                            20

<210> SEQ ID NO 12
<211> LENGTH: 19
<212> TYPE: DNA
<213> ORGANISM: Artificial Sequence
<220> FEATURE:
<223> OTHER INFORMATION: SYNTHETIC

<400> SEQUENCE: 12
taggtggtct cgtgaatgc                                             19

<210> SEQ ID NO 13
<211> LENGTH: 24
<212> TYPE: DNA
<213> ORGANISM: Artificial Sequence
<220> FEATURE:
<223> OTHER INFORMATION: SYNTHETIC

<400> SEQUENCE: 13
tctctgaagc tgcaagtgat ttac                                       24

<210> SEQ ID NO 14
<211> LENGTH: 24
<212> TYPE: DNA
<213> ORGANISM: Artificial Sequence
<220> FEATURE:
<223> OTHER INFORMATION: SYNTHETIC

<400> SEQUENCE: 14
aatctgggtc attctcctga ttgg                                       24

<210> SEQ ID NO 15
<211> LENGTH: 163
<212> TYPE: DNA
<213> ORGANISM: Artificial Sequence
<220> FEATURE:
<223> OTHER INFORMATION: SYNTHETIC

<400> SEQUENCE: 15
gacagcgtga ggagaagtcc aagggaggaa tgctgcaaca acgcctcttt cagacgctgc    60
aacttcgagg aagtcgccga atattgcatc gagctgcgtc ccggcgttaa cacctgcagt   120
tccaggtagg aggtctcaag gatcatcccg tccctgtcct ata                    163

<210> SEQ ID NO 16
<211> LENGTH: 22
<212> TYPE: DNA
<213> ORGANISM: Artificial Sequence
<220> FEATURE:
<223> OTHER INFORMATION: SYNTHETIC

```
<400> SEQUENCE: 16
tcccgtccct gtcctatact tg                                          22

<210> SEQ ID NO 17
<211> LENGTH: 22
<212> TYPE: DNA
<213> ORGANISM: Artificial Sequence
<220> FEATURE:
<223> OTHER INFORMATION: SYNTHETIC

<400> SEQUENCE: 17
cggtgatttg actttgagca tc                                          22

<210> SEQ ID NO 18
<211> LENGTH: 21
<212> TYPE: DNA
<213> ORGANISM: Artificial Sequence
<220> FEATURE:
<223> OTHER INFORMATION: SYNTHETIC

<400> SEQUENCE: 18
gaaacggcta ccacatccaa g                                           21

<210> SEQ ID NO 19
<211> LENGTH: 20
<212> TYPE: DNA
<213> ORGANISM: Artificial Sequence
<220> FEATURE:
<223> OTHER INFORMATION: SYNTHETIC

<400> SEQUENCE: 19
gattgggtaa tttgcgtgcc                                             20

<210> SEQ ID NO 20
<211> LENGTH: 20
<212> TYPE: DNA
<213> ORGANISM: Artificial Sequence
<220> FEATURE:
<223> OTHER INFORMATION: SYNTHETIC

<400> SEQUENCE: 20
taatacgact cactataggg                                             20

<210> SEQ ID NO 21
<211> LENGTH: 21
<212> TYPE: DNA
<213> ORGANISM: Artificial Sequence
<220> FEATURE:
<223> OTHER INFORMATION: SYNTHETIC

<400> SEQUENCE: 21
atgggatact ggaatgccga g                                           21

<210> SEQ ID NO 22
<211> LENGTH: 21
<212> TYPE: DNA
<213> ORGANISM: Artificial Sequence
<220> FEATURE:
<223> OTHER INFORMATION: SYNTHETIC

<400> SEQUENCE: 22
ctggaactgc aggtgttaac g                                           21

<210> SEQ ID NO 23
<211> LENGTH: 21
<212> TYPE: DNA
```

```
<213> ORGANISM: Artificial Sequence
<220> FEATURE:
<223> OTHER INFORMATION: SYNTHETIC

<400> SEQUENCE: 23
atgggatact ggaatgccga g                                              21

<210> SEQ ID NO 24
<211> LENGTH: 21
<212> TYPE: DNA
<213> ORGANISM: Artificial Sequence
<220> FEATURE:
<223> OTHER INFORMATION: SYNTHETIC

<400> SEQUENCE: 24
ctggaactgc aggtgttaac g                                              21

<210> SEQ ID NO 25
<211> LENGTH: 18
<212> TYPE: DNA
<213> ORGANISM: Artificial Sequence
<220> FEATURE:
<223> OTHER INFORMATION: SYNTHETIC

<400> SEQUENCE: 25
atggtgagca agggcgag                                                  18

<210> SEQ ID NO 26
<211> LENGTH: 19
<212> TYPE: DNA
<213> ORGANISM: Artificial Sequence
<220> FEATURE:
<223> OTHER INFORMATION: SYNTHETIC

<400> SEQUENCE: 26
tgtacagctc gtccatgcc                                                 19

<210> SEQ ID NO 27
<211> LENGTH: 18
<212> TYPE: DNA
<213> ORGANISM: Artificial Sequence
<220> FEATURE:
<223> OTHER INFORMATION: SYNTHETIC

<400> SEQUENCE: 27
atggtgagca agggcgag                                                  18

<210> SEQ ID NO 28
<211> LENGTH: 17
<212> TYPE: DNA
<213> ORGANISM: Artificial Sequence
<220> FEATURE:
<223> OTHER INFORMATION: SYNTHETIC

<400> SEQUENCE: 28
tgtacagctc gtccatg                                                   17

<210> SEQ ID NO 29
<211> LENGTH: 19
<212> TYPE: DNA
<213> ORGANISM: Artificial sequence
<220> FEATURE:
<223> OTHER INFORMATION: SYNTHETIC

<400> SEQUENCE: 29
gccttgcagt catccttga                                                 19
```

-continued

```
<210> SEQ ID NO 30
<211> LENGTH: 20
<212> TYPE: DNA
<213> ORGANISM: Artificial sequence
<220> FEATURE:
<223> OTHER INFORMATION: SYNTHETIC

<400> SEQUENCE: 30
aggccggaga gaagaatgtt                                                    20

<210> SEQ ID NO 31
<211> LENGTH: 21
<212> TYPE: DNA
<213> ORGANISM: Artificial sequence
<220> FEATURE:
<223> OTHER INFORMATION: SYNTHETIC

<400> SEQUENCE: 31
ccctaaacga tgctgactag c                                                  21

<210> SEQ ID NO 32
<211> LENGTH: 19
<212> TYPE: DNA
<213> ORGANISM: Artificial sequence
<220> FEATURE:
<223> OTHER INFORMATION: SYNTHETIC

<400> SEQUENCE: 32
tacccccgga actcaaaga                                                     19

<210> SEQ ID NO 33
<211> LENGTH: 518
<212> TYPE: RNA
<213> ORGANISM: Macrobrachium rosenbergii

<400> SEQUENCE: 33
cuggaacugc aggguguuaac gccgggacgc agcucgaugc aauauucggc gacuuccucg        60
aaguugcagc gucugaaaga ggcguuguug cagcauuccu cccuuggacu ucuccucacg        120 cgucccucc ggaagcgacg cuucgaaugc agcauauugu cgcuucuuc ccugcucagc         180 gucaugugcu gaaucuccuc cuccaccuua gauaccuucu gaguuucuuc gucagccaug        240
gucaaguggg uagcucucgg guggcgagc gauggagacu ucguagaagg aacgguauag        300
augucagcag aucgucgcuc uuuggaaacg uagguggguc cugggttgau guaguuguug        360
ugucucaggc agacggaggc aaggguguuc guuaugcgc cgcagucaaa gucaacggag        420
aggcauucga ucucauagcu cgaagaaggu ugagggagaa gcgaugcuac gagugagcag        480
aacaacacac acuugaucuc ggcauuccag uaucccau                                518

<210> SEQ ID NO 34
<211> LENGTH: 518
<212> TYPE: RNA
<213> ORGANISM: Macrobrachium rosenbergii

<400> SEQUENCE: 34
augggauacu ggaaugccga gaucaagugu guuguuucu gcucacucgu agcaucgcuu         60
cucccucaac cuucuucgag cuaugagauc gaaugcccuc ccguugacuu ugacugcggc       120
gacauaacga acacccuugc cuccgucugc cugagacaca acaacuacau caacccagga       180
cccaccuacg uuccaaaaga gcgacgaucu gcgacaucu auaccguucc uucuacgaag        240
ucuccaucgc ucgcccaccc gagagcuacc cacuugacca uggcugacga agaaacucag       300
```

```
aagguaucua  agguggagga  ggagauucag  cacaugacgc  ugagcaggga  agaagcgaac      360
aauaugcugc  auucgaagcg  ucgcuuccgg  agggacagcg  ugaggagaag  uccaagggag      420
gaaugcugca  acaacgccuc  uuucagacgc  ugcaacuucg  aggaagucgc  cgaauauugc      480
aucgagcugc  gucccggcgu  uaacaccugc  aguuccag                                518
```